US009770893B2

(12) United States Patent
Lange et al.

(10) Patent No.: US 9,770,893 B2
(45) Date of Patent: *Sep. 26, 2017

(54) METHOD FOR MAINTAINING A FASTENER IN A FOLDED CONFIGURATION

(71) Applicant: The Procter & Gamble Company, Cincinnati, OH (US)

(72) Inventors: Stephen Joseph Lange, Cincinnati, OH (US); Mark James Kline, Okeana, OH (US); Jay Tao, Mason, OH (US); Ebrahim Rezai, Mason, OH (US); James David Landgrebe, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 137 days.

This patent is subject to a terminal disclaimer.

(21) Appl. No.: 14/837,238

(22) Filed: Aug. 27, 2015

(65) Prior Publication Data

US 2015/0360458 A1    Dec. 17, 2015

Related U.S. Application Data

(63) Continuation of application No. 14/258,106, filed on Apr. 22, 2014, now Pat. No. 9,144,963, which is a
(Continued)

(51) Int. Cl.
*A61F 13/15* (2006.01)
*B32B 38/18* (2006.01)
(Continued)

(52) U.S. Cl.
CPC ........ *B32B 38/18* (2013.01); *A61F 13/15756* (2013.01); *A61F 13/581* (2013.01);
(Continued)

(58) Field of Classification Search
None
See application file for complete search history.

(56) References Cited

U.S. PATENT DOCUMENTS

| 3,860,003 A | 1/1975 | Buell |
| 4,200,963 A | 5/1980 | Kamfe |

(Continued)

FOREIGN PATENT DOCUMENTS

| EP | 1350497 | 10/2003 |
| WO | WO 92/22273 | 12/1992 |

(Continued)

OTHER PUBLICATIONS

International Search Report and Written Opinion, PCT/US2010/045678, mailed Nov. 30, 2010, 10 pages.
(Continued)

*Primary Examiner* — Barbara J Musser
(74) *Attorney, Agent, or Firm* — James T. Fondriest; Kathleen Y. Carter

(57) ABSTRACT

A method for folding a fastener during a high speed manufacturing process and maintaining the fastener in a folded configuration throughout the high speed manufacturing process. The method includes obtaining an article that has a foldable fastener and moving the article in the machine direction during the high speed manufacturing process. The foldable fastener has first and second opposing surfaces, a web and at least one engaging member joined to the web. The method includes applying a frangible bonding agent to a first portion of the first surface of the fastening system; folding the fastening system such that the frangible bonding agent contacts a second portion of the first surface of the fastening system; and allowing the frangible bonding agent to cool at a temperature of less than 60° C.

11 Claims, 15 Drawing Sheets

Related U.S. Application Data continuation of application No. 13/716,271, filed on Dec. 17, 2012, now Pat. No. 8,741,086, which is a continuation of application No. 12/794,130, filed on Jun. 4, 2010, now Pat. No. 8,753,467.

(60) Provisional application No. 61/235,456, filed on Aug. 20, 2009, provisional application No. 61/184,102, filed on Jun. 4, 2009.

(51) Int. Cl.
| | | |
|---|---|---|
| *A61F 13/58* | (2006.01) | |
| *A61F 13/62* | (2006.01) | |
| *B32B 37/10* | (2006.01) | |
| *B32B 37/14* | (2006.01) | |
| *B32B 37/12* | (2006.01) | |
| *B32B 38/00* | (2006.01) | |

(52) U.S. Cl.
CPC ............ *A61F 13/62* (2013.01); *A61F 13/625* (2013.01); *B32B 37/10* (2013.01); *B32B 37/1036* (2013.01); *B32B 37/12* (2013.01); *B32B 37/144* (2013.01); *B32B 37/1292* (2013.01); *B32B 38/0004* (2013.01); *B32B 2037/1215* (2013.01); *B32B 2305/20* (2013.01); *B32B 2309/02* (2013.01); *B32B 2309/10* (2013.01); *B32B 2310/024* (2013.01); *B32B 2310/0843* (2013.01); *B32B 2555/02* (2013.01); *Y10T 156/1049* (2015.01); *Y10T 156/1051* (2015.01)

(56) References Cited

U.S. PATENT DOCUMENTS

| | | |
|---|---|---|
| 4,209,563 A | 6/1980 | Sisson |
| 4,525,407 A | 6/1985 | Ness |
| 4,662,875 A | 5/1987 | Hirotsu |
| 4,834,741 A | 5/1989 | Sabee |
| 4,846,815 A | 7/1989 | Scripps |
| 4,894,060 A | 1/1990 | Nestegard |
| 5,032,122 A | 7/1991 | Noel |
| 5,143,679 A | 9/1992 | Weber |
| 5,151,092 A | 9/1992 | Buell |
| 5,156,793 A | 10/1992 | Buell |
| 5,221,274 A | 6/1993 | Buell |
| 5,256,717 A | 10/1993 | Stauffer |
| 5,326,612 A | 7/1994 | Goulait |
| 5,330,458 A | 7/1994 | Buell |
| 5,518,801 A | 5/1996 | Chappell |
| 5,554,145 A | 9/1996 | Roe |
| 5,569,234 A | 10/1996 | Buell |
| 5,571,096 A | 11/1996 | Dobrin |
| 5,580,411 A | 12/1996 | Nease |
| 5,650,214 A | 7/1997 | Anderson |
| 5,865,823 A | 2/1999 | Curro |
| 5,938,648 A | 8/1999 | LaVon |
| 6,004,306 A | 12/1999 | Robles |
| 6,432,098 B1 | 8/2002 | Kline |
| 6,476,289 B1 | 11/2002 | Buell |
| 6,701,580 B1 | 3/2004 | Bandyopadhyay |
| 7,416,545 B1 | 8/2008 | Kline |
| 7,717,150 B2 | 5/2010 | Manabe |
| 7,820,003 B2 | 10/2010 | Tachibana et al. |
| 8,741,086 B2 | 6/2014 | Lange et al. |
| 8,753,467 B2 | 6/2014 | Lange et al. |
| 9,144,963 B2 * | 9/2015 | Lange ............... A61F 13/15756 |
| 2005/0208854 A1 | 9/2005 | Sadato |
| 2008/0044616 A1 | 2/2008 | Hanao |
| 2008/0050555 A1 | 2/2008 | Sadato |
| 2008/0097368 A1 | 4/2008 | Molander |
| 2008/0208152 A1 | 8/2008 | Eckstein et al. |
| 2008/0262459 A1 | 10/2008 | Kamoto |
| 2008/0312627 A1 | 12/2008 | Takeuchi |
| 2009/0004435 A1 | 1/2009 | Hanao |
| 2010/0307668 A1 | 12/2010 | Lange et al. |
| 2013/0098530 A1 | 4/2013 | Lange et al. |
| 2014/0224412 A1 | 8/2014 | Lange et al. |

FOREIGN PATENT DOCUMENTS

| | | |
|---|---|---|
| WO | WO 99/11211 | 3/1999 |
| WO | WO 99/11212 | 3/1999 |
| WO | WO 02/056814 | 7/2002 |
| WO | WO 03/105740 | 12/2003 |
| WO | WO 2007/004640 | 1/2007 |
| WO | WO 2007/036908 | 4/2007 |
| WO | WO 2007/069227 | 6/2007 |
| WO | WO 2007/072386 | 6/2007 |
| WO | WO 2007/072421 | 6/2007 |

OTHER PUBLICATIONS

Hot-melt adhesive from Wikipedia http://en.wikipedia.org/wik/Hot-melt_adhesive, no date.

* cited by examiner

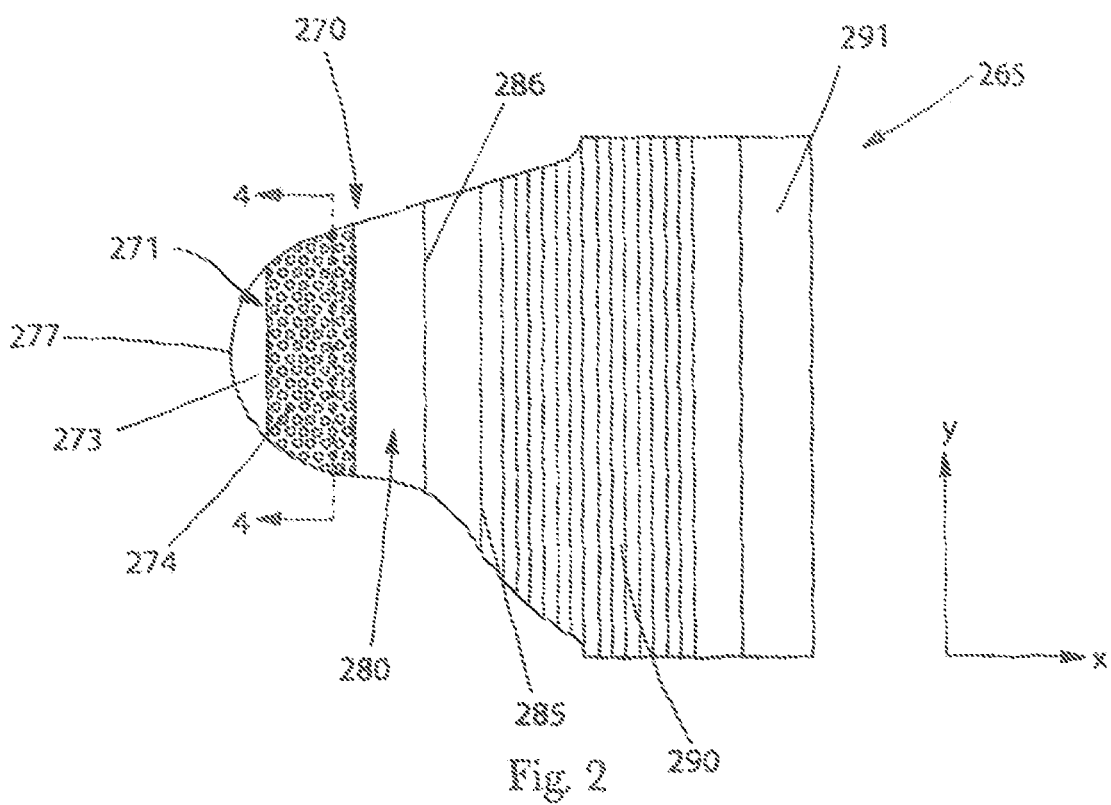

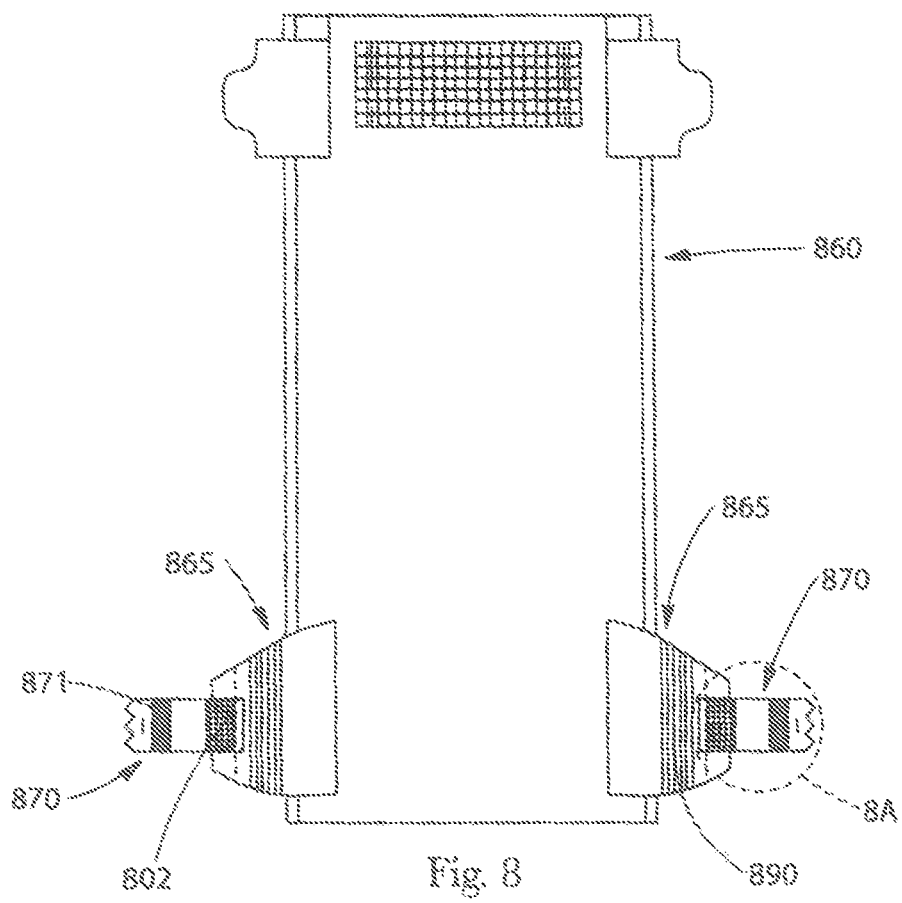
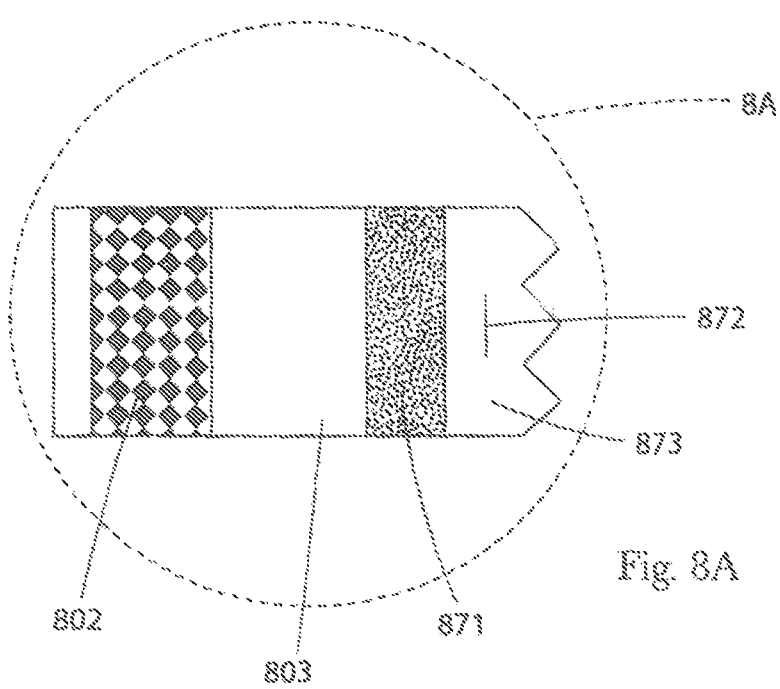

METHOD FOR MAINTAINING A FASTENER IN A FOLDED CONFIGURATION

FIELD OF THE INVENTION

A method for processing a disposable absorbent article on a high speed manufacturing line is disclosed. More specifically, a method for maintaining a disposable absorbent article fastener in a folded configuration with a frangible bonding agent is disclosed.

BACKGROUND OF THE INVENTION

Wearable absorbent articles (e.g., taped diapers, pull-on diapers, training pants, sanitary napkins, panty liners, incontinence briefs, and bandages) typically offer the benefit of receiving and containing the bodily exudates of a wearer. Disposable varieties of such absorbent articles are commonly known, and are typically mass produced on a high speed production line. Some disposable absorbent articles include a mechanical fastening system (e.g., hook/loop or tab/slot) for maintaining the article in a desired position or configuration prior to, during, and/or after use of the article. Such fastening systems may include one or more elements that extend laterally outwardly beyond the side edges of the article, such as commonly known fastening tabs. These laterally outwardly extending portions of the fastening system may increase the risk of contamination or damage to the article, an article element, and/or the manufacturing equipment during a high speed manufacturing process. Repositioning the outwardly extending portions of the fastening system (e.g., by folding the portion laterally inward) may reduce the likelihood of damage or contamination, but the folded fastening system element may not remain suitably folded for a desired amount of time (e.g., the duration of the manufacturing process) due to the high speed nature of the manufacturing process. For example, relatively high velocities on the manufacturing line can lead to fasteners unfolding due to centrifugal forces and bending stresses as the fasteners travel around rollers. In addition, the fasteners may collide with stationary parts of the machine at high speeds, causing the fastening tabs to open and leaving them vulnerable to being crushed or damaged by other rotating or stationary equipment.

A fastening system that includes a mechanical fastener having commonly known hooks or other similar features may be maintained in a folded configuration by engaging the mechanical fastener with a complementary element of the fastening system, such as loops or a nonwoven portion. Such mechanical fastening systems are generally engaged by entangling the hooks or other similar feature with the complementary element. However, an engaged mechanical fastener still may not provide sufficient bonding strength to maintain the fastener in the desired folded configuration during a high speed manufacturing process. Therefore, in order to increase the bond strength of the mechanical fastener, a bonding agent such as an adhesive may be applied to one or more portions of the mechanical fastener prior to folding and/or engaging the fastening system. Conventional adhesives such as commonly known hot-melt adhesives generally form permanent bonds. The bond strength provided by such permanent bonding agents is relatively high, and may even increase from the time the absorbent article is made and the time it is purchased and/or used by a consumer due to the effects of high temperatures associated with shipping and/or storage of the article. While permanent bonding agents may provide the desired bond strength during a high speed manufacturing process, the increased bond strength and/or infrangibility of the adhesive bond may be undesirable at other times such as when a consumer attempts to use the article or fastening system and it becomes necessary to break the bond. In order for a disposable absorbent article to be used as intended by a consumer, it may be necessary or desirable to unfold or reposition the fastening system or other portion of the article. Thus, the use of a permanent bonding agent may undesirably increase the difficulty associated with unfolding or repositioning the fastener or other article portion. In addition, mechanical fastening systems are typically configured to be refastenable (i.e., the fastener can be fastened and unfastened more than once without substantial loss of fastening capability). Applying a permanent bonding agent to the mechanical fastener may undesirably reduce the refastenability of the mechanical fastener, for example, by covering up the engageable portions of the mechanical fastener with fibers or other material or even melting the engaging elements.

One way to address the high bond strength problems described above may be to use a temporary bonding agent such as a temporary strength adhesive to maintain the fastening system in a folded configuration. Temporary strength adhesives, sometimes referred to as "fugitive" adhesives, are known (see, e.g., U.S. Publication No. 2006/0027320, filed by Kueppers, et al., on Jun. 20, 2005). However, fugitive adhesives are typically used to create temporary, frangible paper-to-paper bonds, for example, for joining cardboard containers and/or portions thereof to one another, or for use with envelopes, labels, and the like. Typically, when the bond provided by a fugitive adhesive is broken, the adhesive is no longer tacky and does not readily adhere to anything. Fugitive adhesives are not known in the art for use in the fastening system of an absorbent article such as a disposable diaper. One reason for this may be the difference in materials used in absorbent articles (which typically include at least some polymeric materials as opposed to only paper). Another reason may be that the fastening system for an absorbent article is generally intended to provide a permanent bond or, in the case of a refastenable fastening system, a quasi-permanent bond to maintain the article in the desired position and/or configuration on a wearer. In other words, one goal of the fastening system is to provide sufficient bond strength to prevent the article from undesirably coming unfastened during the intended use of the article, and a temporary bonding agent will typically not help achieve this goal.

In addition, known fugitive adhesives may not form a strong enough initial bond to make them capable of holding folded portions of absorbent articles in place during a high speed manufacturing process, during which time the folded portions of the absorbent articles could come in to contact with other objects in the manufacturing process. For example, water-based fugitive adhesives, which are typically used in labeling and envelope applications, have relatively low bond strengths when wet (i.e., when applied), and while this may be sufficient for use in bonding paper to paper, it is generally not sufficient for the absorbent article applications described herein. Further, in order for conventional fugitive adhesives to lose strength, some fugitive adhesives may require active heating, radiation, or the like to reduce their strength, all of which are impractical for use with absorbent articles. Other known fugitive adhesives are solvent cross-linked materials, which may not be suitable for use in an article that contacts the skin of a user.

Accordingly, it would be desirable to provide a method for folding a fastener and maintaining the fastener in a folded configuration during a high speed manufacturing process. It would also be desirable to provide an article comprising a folded fastening system that is relatively easy to unfold by a consumer. It would further be desirable to provide a folded fastening system which does not exhibit impaired fastenability or refastenability after the fastener is unfolded.

SUMMARY OF THE INVENTION

In order to provide a solution to the problems set forth above, at least one embodiment described herein provides a method for folding a fastener during a high speed manufacturing process and maintaining the fastener in a folded configuration throughout the high speed manufacturing process. The method comprises obtaining an article comprising a foldable fastener and moving the article in the machine direction during the high speed manufacturing process. The high speed manufacturing process has a cross direction orthogonal to the machine direction. The foldable fastener comprises first and second opposing surfaces, a web, and at least one engaging member joined to the web. The method also comprises applying a frangible bonding agent to a first portion of the first surface of the fastening system. The method further comprises folding the fastening system such that the frangible bonding agent contacts a second portion of the first surface of the fastening system, and allowing the frangible bonding agent to cool at a temperature of less than 60° C.

BRIEF DESCRIPTION OF THE FIGURES

FIG. 2 is a top plan view of an ear and a fastening tab.
FIG. 8 is a top plan view of a disposable absorbent article.
FIG. 8A is a detailed view of a fastening tab.

DETAILED DESCRIPTION OF THE INVENTION

Definitions

Figure 1:
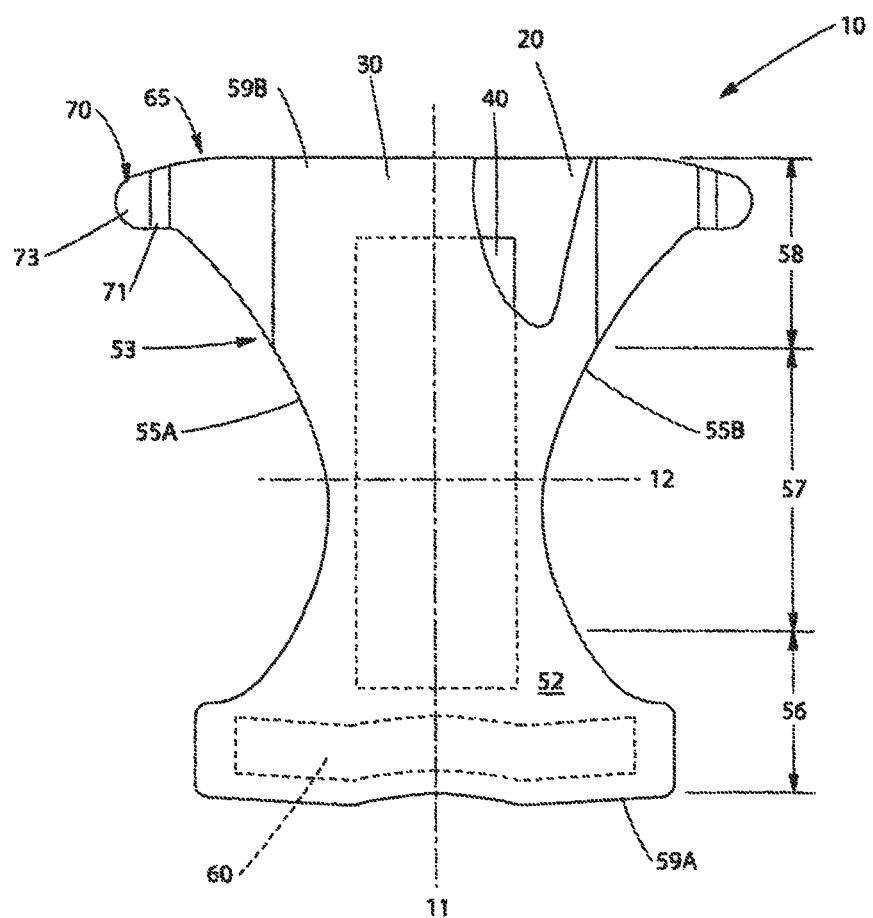
FIG. 1 is a partial cut-away, top plan view of a disposable absorbent article.

"Absorbent article" means an article that absorbs and/or contains liquid. Wearable articles are articles placed against or in proximity to the body of a wearer, Wearable absorbent article are absorbent articles placed against or in proximity to the body of a wearer to absorb and contain various exudates discharged from the body. Nonlimiting examples of wearable absorbent articles include diapers, pant-like or pull-on diapers, training pants, sanitary napkins, tampons, panty liners, incontinence devices, and the like.

"Comprising" means that the various components, ingredients, or steps, can be conjointly employed in practicing the disclosed fastening system process. Accordingly, the term "comprising" encompasses the more restrictive terms "consisting essentially of" and "consisting of."

"Disposable" means absorbent articles which generally are not intended to be laundered or otherwise restored or reused as an absorbent article (i.e., they are intended to be discarded after a single use and, preferably, to be recycled, composted or otherwise disposed of in an environmentally compatible manner).

"Disposed" means the placement of one element of an article relative to another element of an article. For example, the elements may be formed (joined and positioned) in a particular place or position as a unitary structure with other elements of an article or as a separate element joined to another element of the article. When one element is disposed on another element, the elements or portions thereof may be in direct contact with one another, or the elements or portions thereof may be separated, for example, by the joining means (e.g., adhesive).

"Engage" and variations thereof mean to join two or more elements to one another in a cooperative fashion. For example, a hook/loop type mechanical fastening system may be engaged by entangling the hooks and loops with one another. In another example, two substrates may be engaged by applying an adhesive to one or both substrates and contacting them with one another. In yet another example, a hook/loop type mechanical fastening system may be engaged by applying an adhesive to the hooks of the fastening system and contacting the adhesive with another element, which may or may not include loops, such that the hook containing portion of the fastening system and the contacted substrate are joined to one another due, at least partially, to the adhesive.

"Elastic" means the property of a material or component (e.g., film, fiber, nonwoven, strand, laminate or combinations of these) to elongate, without rupture or breakage, by at least 50% at a load of between 0.1 and 10 N/cm in the Hysteresis Test described in detail in copending U.S. application Ser. No. 12/398,615. Further, upon release of the load, the elastic material or component has set less than or equal to 20% as measured according to the aforementioned Hysteresis Test. For example, an elastic material that has an initial length of 25 mm can elongate to at least 37.5 mm (50% elongation) and, upon removal of the force, retract to a length of 27.5 mm, i.e., have a set of 2.5 mm (10% set). It is to be understood, however, that this definition of elastic does not apply to materials such as individual elastic strands that do not have the proper dimensions (e.g., not wide enough) to be properly subjected to the hysteresis test. Instead, such material is considered to be elastic if it can elongate to at least 50% upon application of a biasing force, and return substantially to its original length (i.e., exhibit less than 20% set) upon release of the biasing force.

"Extensible" material is material that elongates, without rupture or breakage, by at least 50% at a load of between 0.1 and 10 N/cm in the Hysteresis Test set forth in copending U.S. application Ser. No. 12/398,615. Further, upon release of the load, the material has greater than 20% set, as measured according to the aforementioned Hysteresis Test. For example, an extensible material that has an initial length of 25 mm can elongate at least to 37.5 mm (50% elongation) and, upon removal of the applied force, retract to a length of 35 mm, i.e., have a set of 10 mm (40% set), when subjected to the aforementioned Hysteresis Test.

"Film" means a substantially nonporous material made by a process that includes extrusion of, e.g., a polymeric material through a relatively narrow slot of a die. A film may be impervious to a liquid and pervious to an air vapor, but need not necessarily be so.

"Foldable" means that a component can be bent such that one portion of the component can be placed over another portion of the same component in an overlaying relationship without permanently altering its ability to function as intended.

"Frangible Bond" means a bond that through deformation tends to break relatively easily via cohesive failure, rather than deforming plastically (i.e., extensibly) and retaining its cohesion as a single object. Frangible bonds are sometimes referred to as being brittle, and are generally designed to be broken by a user at some point during the use of an article comprising the frangible bond.

"High speed manufacturing process" means a manufacturing process that is capable of producing more than 400 products per minute.

"Joined" means configurations whereby an element is directly secured to another element by affixing the element directly to the other element (e.g., ultrasonic bonding, thermal bonding, high pressure bonding and the like), and configurations whereby an element is indirectly secured to another element by affixing the element to intermediate member(s) that in turn are affixed to the other element (e.g., adhesive bonding where the adhesive is the intermediate member).

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" ("MD") is the direction parallel to the direction of travel of the web in a manufacturing process. Directions within 45 degrees of the MD are considered to be machine directional. The "cross machine direction" ("CD") is the direction substantially perpendicular to the MD and in the plane generally defined by the web. Directions within 45 degrees of the CD are considered to be cross directional.

"Nonwoven" means a porous, fibrous material made from continuous (long) filaments (fibers) and/or discontinuous (short) filaments (fibers) by processes such as spunbonding, meltblowing, carding, and the like. Nonwovens do not have a woven or knitted filament pattern. Nonwovens may be liquid permeable or impermeable.

"Outboard" and "inboard" mean, respectively, the location of an element disposed relatively far from or near to the longitudinal centerline of an absorbent article with respect to a second element. For example, if element A is outboard of element B, then element A is farther from the longitudinal centerline than is element B. Similarly, "outward" and "inward" mean, respectively, directions which are away from or toward the longitudinal centerline.

"Refastenable" means the ability of two or more elements or portions of elements, which are fastened together, to be unfastened and refastened without substantial degradation of fastener performance or damage to surrounding components of the article that would impair the article's continued use.

"Web" means a material capable of being wound into a roll. Webs may be films, nonwovens, laminates, apertured laminates, and the like.

"X-Y plane" means the plane defined by the MD and CD of a moving web or the length and width of a piece of material.

Disposable Absorbent Article

FIG. 1 shows a partial cut-away, plan view of a diaper 10 in a flat-out, uncontracted state (i.e., with no elastic induced contraction). Portions of FIG. 1 are cut away to more clearly show the construction of the diaper 10. The diaper 10 may also include a first waist region 56, a second waist region 58, and a crotch region 57 disposed therebetween. The diaper 10 may have a periphery 53 defined by opposing longitudinal side edges 55A and 55B and opposing end edges 59A and 59B. The inner, wearer-facing surface 52 of the diaper 10 is oriented towards the viewer and the opposing outer, garment-facing surface is oriented away from the viewer. As shown in FIG. 1, the diaper 10 may include a liquid pervious topsheet 30; a liquid impervious outer cover 20 joined with at least a portion of the topsheet 30, for example, along the periphery 53 of the diaper 10; and an absorbent core assembly 40 positioned between the topsheet 30 and the outer cover 20. The diaper 10 may include an elastic waist feature 60 and a fastening system. The fastening system may include an ear 65 joined to at least one waist region 56 and/or 58. In certain embodiments, the ear 65 and one or both waist regions 56 and/or 58 may be formed from as a unitary structure. The ear 65 may include a fastening tab 70, which extends laterally outwardly from the diaper 10 and an engaging member 71 disposed on the fastening tab 70. The engaging member 71 may be engageable with another portion of the diaper 10 (e.g., another portion of the ear 65 and/or a receiving member). "Engageable" means one element is configured to be joined to another element, for example, through the creation of an entanglement-type mechanical bond. The fastening tab 70 may include a gripping portion 73 that enables a user to grasp and/or manipulate the fastening tab 70. The gripping portion 73 may extend laterally outwardly from the edge of the engaging member 71 at a distance of greater than 0 mm, for example between 0 and 20 mm. The inner, wearer-facing surface 52 of the diaper 10 may include at least a portion of the topsheet 30 and other components, which may be joined to the topsheet 30. The outer, garment-facing surface may include at least a portion of the outer cover 20 and other components, which may be joined to the outer cover 20. The diaper may include a longitudinal centerline 11 and a lateral centerline 12 orthogonal thereto. Nonlimiting examples of absorbent articles and absorbent article components are described generally in U.S. Pat. Nos. 3,860,003; 5,151,092; 5,221,274; 5,554,145; 5,569,234; 5,580,411; 6,004,306; 5,938,648; 5,865,823; and 5,571,096.

Fastening System

Known mechanical fastening systems (i.e., fastening systems that form mechanical bonds between themselves and/or another component when fastened) include hook/loop type mechanical fastening systems and tab/slot type mechanical fastening systems. Other examples of mechanical fastening systems include, without limitation, hermaphroditic, friction, static, magnetic, button/button hole, zippers, buckles and the like. Examples of mechanical fastening systems and configurations of mechanical fastening systems may be found in U.S. Pat. Nos. 4,662,875; 4,846,815; 4,894,060;

and 6,432,098; and PCT Publication No. WO92/022273. Hook/loop type mechanical fastening systems typically includes an engaging member comprising hooks and a complementary receiving member comprising loops. The hooks engage the loops, typically through entanglement, to form a mechanical bond. In certain embodiments, the engaging member may comprise a base for providing a relatively strong backing that the hooks can be imbedded, bonded, woven or fused into. The hooks and the base may be formed from a single piece of material (e.g., as described in U.S. Pat. No. 6,478,784 issued to Johnson, et al.), or the hooks and the base may be discrete components that have been joined to one another by any means known in the art. The base or portions thereof may be flexible or stiff, as desired, for example, by including a stiffening element. The base may be manufactured from a wide variety of materials commonly used for backings for mechanical fasteners (e.g., nylon, polypropylene, polyethylene, or any equivalent material or blends of these materials). In certain embodiments, the base may be a woven nylon material secured to a nonwoven or a film member by an adhesive and/or other commonly known bonding means. The base may have an engaging side and a non-engaging side opposed thereto. The non-engaging side of the base may be permanently joined to a fastening tab or another component of the absorbent article, such as a waist panel, side panel, or ear. The hooks generally project out of the engaging side of the base, and each hook has a proximal end joined to the engaging side of the base and a distal end spaced away from the proximal end. The distal and proximal ends of the hook may be connected with a stem that extends between the two ends. The shape of the hooks may be selected to provide a suitable amount of entanglement with complementary receiving elements. Nonlimiting examples of suitable engaging element shapes include hook-shaped, mushroom-shaped, and t-shaped. Suitable examples of engaging member materials include commercially available hook material from Aplix, sold under the product codes 963, 960, 957, and 942, and 3M, sold under the product codes CS200, CS300, CS600, or MC6. One example of a suitable receiving member material is sold by 3M as product code KLT. Another example of suitable receiving member material is product #18904 sold by Guilford located in Wilmington, N.C. In certain embodiments, the receiving member may simply be a nonwoven web (e.g., a single layer of nonwoven or a laminate with at least one nonwoven surface or surface portion). Nonwovens are typically formed from a multitude of fibers arranged in a substantially random pattern. This random arrangement of fibers may provide sufficient loop formations or other similar features on the surface of the nonwoven, which are capable of desirably engaging with the engaging elements (e.g., hooks) of an engaging member. Suitable examples of mechanical fastening systems and elements thereof are disclosed in U.S. Provisional Ser. No. 61/184,102, filed on Jun. 4, 2009 by Kline. U.S. Pat. Nos. 5,032,122, 5,326,612, and 7,416,545; and PCT Publication Nos. WO07/096841, WO07/096842, WO96/022065, WO96/004812 WO07/072421, WO07/072386, and WO07/069227. WO07/036908; WO03/105740, WO99/11211 and WO99/11212.

FIG. 2 shows an exemplary embodiment of an ear 265 for use with, for example, a disposable absorbent article. The ear 265 may include a fastening tab 270 that extends laterally outwardly from the ear 265. The fastening tab 270 may include an engaging member 271, which includes a plurality of engaging elements 274, and a gripping portion 273 that extends laterally outwardly from the engaging member 271 (i.e., in the x-direction) to define the outer edge 277 of the fastening tab 270. The engaging elements 274 may have a frangible bonding agent 230 disposed thereon. In certain embodiments, the frangible bonding agent 230 may be applied to another portion of the ear 265 (e.g., the corrugated portion 290, attachment edge 291, and/or in the vicinity of folding lines 285 and/or 286) such that the engaging elements 274 may be contacted with the frangible bonding agent 230 by folding the ear 265 and/or fastening tab 270. Alternatively or in addition to the embodiments described above, the frangible bonding agent 230 may be applied to the gripping portion 273, for example, by using more than one applicator (e.g., a first glue gun for applying the frangible bonding agent 230 to a first location and a second glue gun for applying the frangible bonding agent 230 to the gripping portion 273 or other second location). The ear 265 may include a support member 280 that supports one or more other elements of the ear 265 and/or fastening tab 270 (e.g., the engaging member 271). The support member 280 may include a nonwoven or film material as the outer layer of an extensible or elastic multilayer laminate structure. In an alternative example, the support member 280 may be formed as a single layer of extensible or elastic nonwoven or film material. In certain embodiments, the support member 280 may include a stiffened region of higher density and/or basis weight material to increase the stability of the fastener when it is engaged (e.g., reduce buckling). The ear 265 may include an attachment edge 291, along which the ear 265 may be joined to an article or article component (e.g., a side panel or absorbent article chassis). The engaging elements 274 are typically engageable with another portion of the ear 265 (e.g., the support member 280 or corrugations 290 formed in the support member 280) and/or receiving elements disposed elsewhere on the article. In certain embodiments, the fastening tab 270 may be folded over itself (e.g., along first folding line 285, second folding line 286, or any other portion of the fastening tab 270 or ear 265, as desired) such that the engaging elements 274 contact at least a portion of the support member 280. In certain embodiments, the fastening tab 270 may be elastic. That is, the fastening tab 270 may be stretched beyond its original length by a tensile force and when the tensile force is removed, the fastening tab 270 exhibits less than 20% set (i.e., exhibits at least 80% recovery). The elasticity of the fastening tab 270 may be provided by a plurality of corrugations 290 formed in the support member 280, for example, by a commonly known incremental stretching process ("activation" or "ring rolling"). Additionally or alternatively, an extensible nonwoven may be joined with an elastic material such as one or more elastic strands and/or an elastic film or nonwoven material to form an elastic laminate material. The nonwoven may be joined to an unstrained (i.e., relaxed) elastic material before, during, or after an activation process to form a so-called zero-strain stretch laminate, or joined to a strained (i.e., stretched) elastic material to form a so-called live-stretch laminate.

Figure 2A:
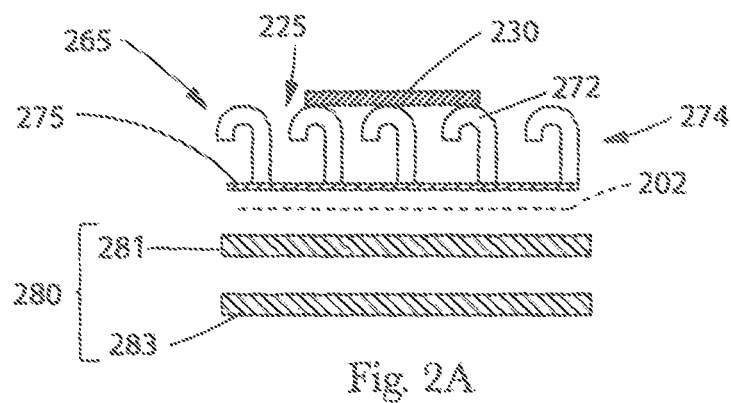
FIG. 2A is schematic cross-section view of a fastening tab.

FIG. 2A shows an exemplary embodiment of a fastening tab 270 along line A-A of FIG. 2. The engaging elements 274 in FIG. 2A are shown as being hook-shaped, however, it is to be understood that the engaging elements 274 may be any suitable shape desired. The fastening tab 270 may include a support member 280 formed as a laminate comprising an upper and a lower nonwoven layer 281 and 283. The fastening tab 270 may include the support member 280 and/or one or more additional nonwoven and/or film components. The base 275 of the engaging member 271 may be joined to the upper nonwoven layer 281, for example, by adhesive layer 202. The bonding agent 230 may be applied to the heads 272 of the engaging elements 274 as a substantially unbroken line that spans the gaps 225 between adjacent engaging elements 274. When the bonding agent 230 is applied as a molten composition, the bonding agent 230 may penetrate at least partially into one or more of the gaps 225, but remains substantially continuous (i.e., unbroken).

Figure 2B:
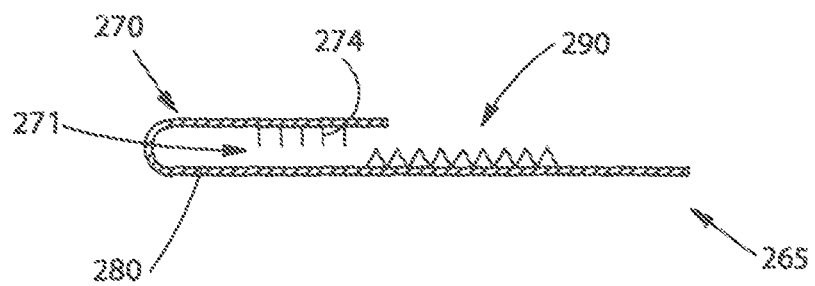
FIG. 2B is schematic cross-section view of a folded ear.

FIG. 2B shows an exemplary embodiment of the ear 265 and fastening tab 270 of FIG. 2 in a folded configuration. As shown in FIG. 2B, the fastening tab 270 is folded over itself in the x-direction along folding line 286. The entire engaging member 271 or a substantial portion thereof (e.g., a majority of the hooks 274) may contact the corrugated portion 290 of the ear 265 in an overlaying configuration. In certain embodiments, however, no portion of the engaging member 271 need contact the corrugated portion 290. The fastening tab 270 and/or ear 265 may be folded in any suitable configuration desired. For example, the fastening tab 270 and/or ear 265 may be folded more than once in the same or different direction(s) (e.g., inwardly and/or outwardly). In certain embodiments, the fastening tab 270 may be folded such that a portion of the fastening tab 270 still extends laterally outwardly past the longitudinal side edge of the article, but to a lesser extent than before it was folded.

Figure 3:
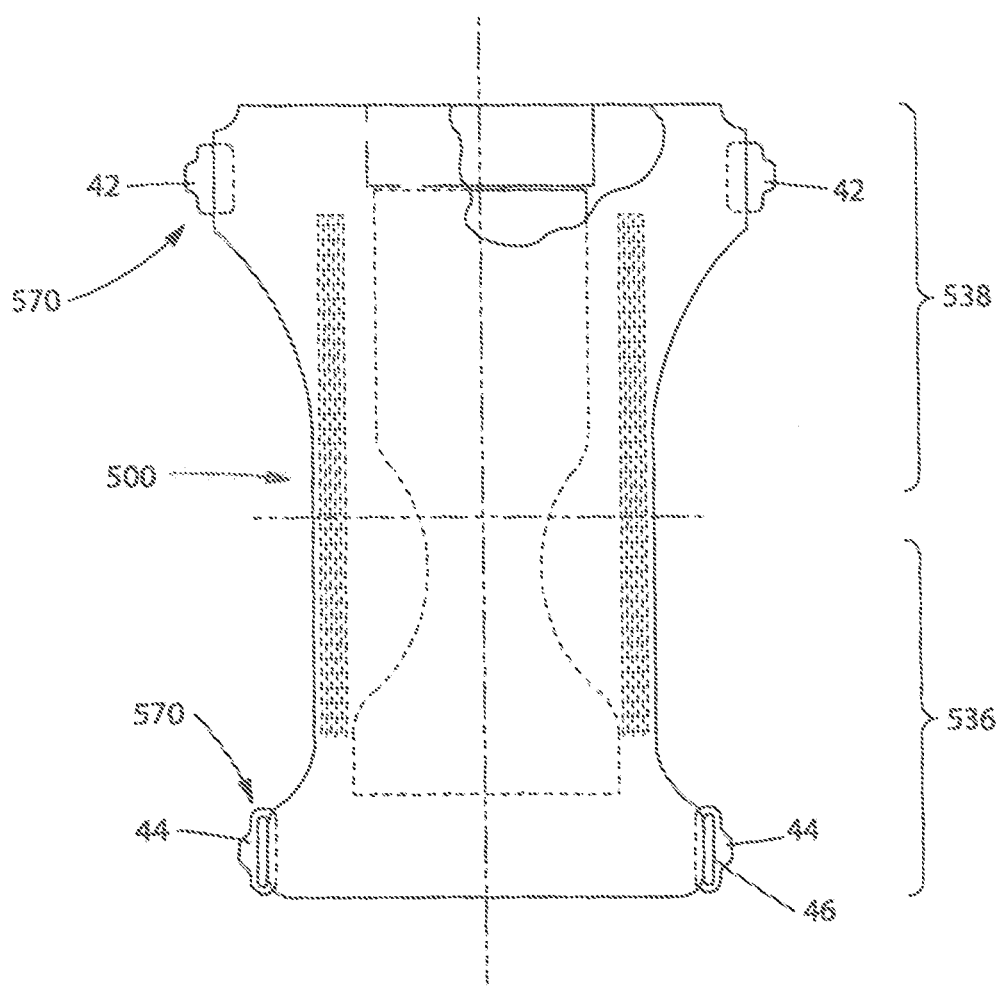
FIG. 3 is a partial cut-away, top plan view of a disposable absorbent article.
Figure 3A:
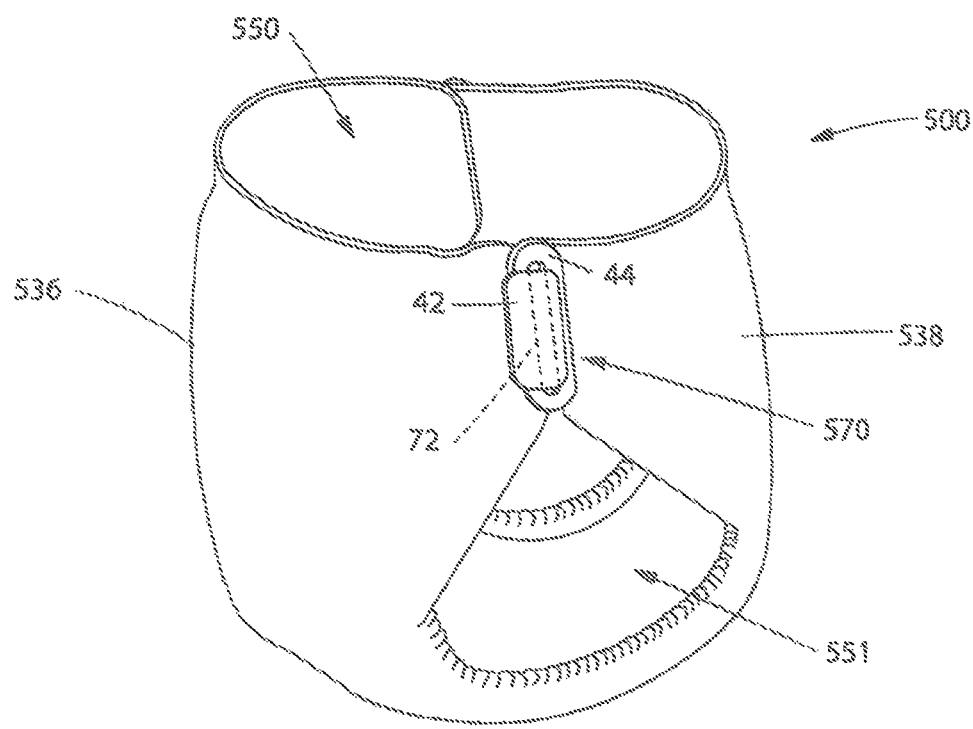
FIG. 3A is a perspective view of a disposable absorbent article.

FIG. 3 shows an exemplary embodiment of a disposable absorbent article 500 in a flat-out, uncontracted state (i.e., with no elastic induced contraction). The article 500 may include a slot/tab type mechanical fastening system 570 positioned at the front and/or rear waist regions 536 and 538. The fastening system 570 may include one or more tab members 42 and one or more slot members 44. The slot members 44 may each have one or more slots 46 configured to pass at least a portion of the tab member 42 therethrough. FIG. 3A shows the disposable absorbent article 500 of FIG. 3 in a fastened configuration (i.e., the fastening system 570 is engaged). As shown in FIG. 3A, at least one of the tab members 42 is passed through a slot 46 of at least one of the slot members 44 to join the front waist region 536 and the rear waist region 538 of the article 500 to one another, thereby providing a waist opening 550 and at least one leg opening 551. The tab members 42 may be joined to the article 500 or a component thereof (e.g., side panel) along a line of attachment 72. The tab member 42 may include a retaining element that helps to keep the fastening system 570 from disengaging. The retaining element may include a raised portion, a lowered portion, a notch, a lip, a rough portion, combinations of these and the like to prevent or at least inhibit the tab member 42 from undesirably slipping back through the slot member 44.

Figure 3B:
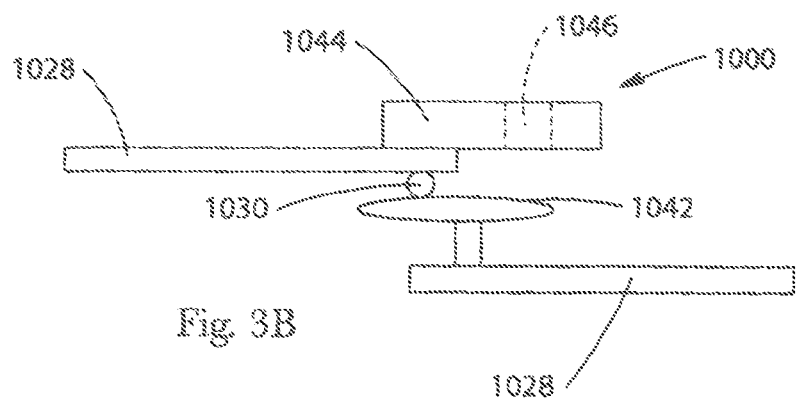
FIG. 3B is a schematic cross-section view of a mechanical fastening system.

FIG. 3B shows an exemplary slot/tab type mechanical fastening system 1000. The fastening system 1000 may include a slot member 1044 and a tab member 1042, each joined to a support member 1028 (e.g., a commonly known nonwoven and/or film material). The slot member includes a slot 1046 configured to pass the tab member 1042 therethrough. The support member 1028 may be joined to or be part of another article component (e.g., a side panel of a disposable diaper). In certain embodiments, the fastening system may include a bonding agent 1030 disposed on a component of the fastening system (e.g., the tab member 1042, the slot member 1044, and/or the support member 1028). For example, the bonding agent 1030 may be disposed on the tab member 1042 such that the tab member 1042 may be joined to itself or another component of the fastening system 1000 (e.g., slot member 1044 and/or support member 1028).

Frangible Bonding Agent

A frangible bonding agent is a bonding agent capable of forming a frangible bond suitable for use in the articles and/or fastening systems disclosed herein. In certain embodiments, the frangible bonding agent may comprise an adhesive such as, for example, a fugitive hot-melt adhesive. A fugitive adhesive is generally understood to be an adhesive that exhibits a decaying bond strength (i.e., has a predictable decrease in bond strength over time). The initial bond strength of a bond formed by a fugitive adhesive is generally limited by the adhesive attraction between the adhesive and the substrate(s) to which it is applied (i.e., the intermolecular attraction between the adhesive and the substrate). However, after a fugitive adhesive crystallizes, the bond strength of the bond is generally limited by the cohesive strength of the adhesive, which is typically less, and in some instances substantially less, than the adhesive strength of the bond. One particularly suitable example of an adhesive for use herein comprises a copolymer of 1-butene in an amount ranging from 10% to 80% by weight based on the weight of the adhesive (e.g., PB-1 available from Basell), wax in an amount of 5% to 60% by weight, based on the weight of the adhesive, and from 55 to 25% of a tackifying resin. It may be desirable to provide the wax as a mixture of high melt point and low melt point waxes in a ratio of 1:7 to 1:1 (high melt point to low melt point). It is believed, without being limited by theory that this ratio may provide a suitable crossover temperature for the adhesive.

Due to the wide range of environmental and processing conditions to which disposable absorbent articles may be exposed, a crossover temperature ($T_x$) of greater than 50° C.; for example, between 50°-70° C.; between 55°-65° C.; between 58°-62° C.; or even 60° C. may be suitable for certain adhesives described herein. $T_x$ is the temperature at which a hot-melt adhesive has the same apparent elastic modulus (G') and apparent viscous modulus (G"). The $T_x$ of an adhesive or other polymeric material may be determined according the Rheological Measurement Test detailed below. At temperatures below the $T_x$ of an adhesive, the adhesive may be more difficult or expensive to process (e.g., the adhesive does not flow as well or at all or additional energy must used), resulting in a smaller process window. Therefore, an adhesive that has a relatively low $T_x$, such as a conventional fugitive adhesive, may have desirable processing characteristics. However, at temperatures above the $T_x$, of such an adhesive, which may occur during transport and/or storage of an article comprising the adhesive, the adhesive may exhibit a greater tendency to flow and may penetrate further into the substrate to which it is applied, thereby causing an undesirable increase in bond strength. It is believed that the bonding agents disclosed herein may provide a solution to this problem. Table 1 below shows a comparison of crossover temperatures for various adhesives.

Fugitive hot-melt adhesives are typically applied to a substrate at a temperature greater than the crossover temperature of the adhesive. Suitable fugitive hot-melt adhesives for use herein may exhibit a peak adhesive bond strength within one hour of application. Once the fugitive hot-melt adhesive cools, it typically begins to crystallize and may exhibit a decaying bond strength. As mentioned above, it is believed, without being limited by theory, that the decaying bond strength is due to the transition of the bond failure mode from adhesive failure to cohesive failure (i.e., the fugitive adhesive forms a frangible bond). Suitable bond strength decays for a fugitive adhesive include a loss of greater than or equal to about any of the following amounts of initial bond strength: 20%, 30%, 40%, 50%, 55%, 60%, 65%, 70%, 75%, 80%, 85%, 90%, 95%, or 100%. The bond strength decay of a fugitive adhesive may be determined according to the Coupon Peel Test described below.

In certain embodiments, a bonding agent that does not form a frangible bond, but exhibits a suitable decaying bonding strength may be used herein. In such embodiments, the bonding agent may fail adhesively or cohesively as long as suitable bonding forces and fastener performance are provided.

Process For Providing an Improved Fastening System.

A frangible bonding agent may be applied to one or more portions of the fastening systems described herein (e.g., the fastening tab, engaging member and/or engaging elements). The fastening system may then be folded such that the frangible bonding agent, by itself or in combination with another fastening mechanism, joins one portion of the fastening system to another portion. For example, a frangible bonding agent may be applied to at least some of the heads of hook-type engaging elements in a hook/loop type fastening system. In such an example, the fastening tab may be folded over such that the frangible bonding agent and optionally the hooks contact another portion of the same surface of the fastening tab. In another example, a frangible bonding agent may be applied to the tab member of a slot/tab type mechanical fastening system, and the tab member may be positioned such that frangible bonding agent contacts the slot member, and/or other portions of the fastening system or article. When applying the frangible bonding agent to a fastening system, it may be desirable to apply the frangible bonding agent such that it does not interfere with the ability of the fastening system to be fastened and/or refastened as intended. For example, applying a frangible bonding agent to a relatively large number of hooks in a refastenable hook/loop type fastening system may interfere with the ability of the hooks to engage with the corresponding loops of the receiving member. Thus, it may be desirable to apply the frangible bonding agent to 10% or less of the hooks (e.g., 9%, 8%, 7%, 6%, 5%, 4%, 3%, 2%, or even less than 1%, but greater than 0%), as measured by the % surface area of the hook-containing portion of the engaging member that includes the frangible bonding agent. The frangible bonding agent may be applied as an unbroken strand or film that extends between two more hooks. In certain embodiments, the frangible bonding agent may be applied as a layer of relatively fine meltblown fibers. The frangible bonding agent may be applied in any suitable linear or nonlinear pattern such as, for example, a pattern that resembles one or more straight lines, one or more broken lines, S-shapes, T-shapes, X-shapes, omega-shapes, dots, circles, rectangles, spirals, combinations of these and the like. In one suitable example, the frangible bonding agent may be applied as substantially straight line (i.e., bead) of fugitive hot-melt adhesive that has a length of between 1% and 100%; 1 and 50%; 1 and 40%; or even 1 and 20% of the length of the engaging member. In order to potentially minimize the effect of the frangible bonding agent on the ability of the fastener to be fastened or refastened, the frangible bonding agent may be applied as a relatively narrow line having a width of between 0.1% and 30%; 1 and 25%; 1 and 15%; or even 1 and 10% of the width of the engaging member. Of course, the frangible bonding agent may have any length or width desired, as long as suitable bond strength and fastener performance is obtained. In certain embodiments, the frangible bonding agent may be contiguous with one or more of the edges of the engaging member and/or fastening system. For example, the frangible bonding agent may extend from one edge of the engaging member to another edge in the MD, CD, and/or diagonally, or the frangible bonding agent may extend from one edge of the engaging member and/or fastening system to an inner portion of the engaging member and/or fastening system (i.e., a portion disposed between two edges), but not to another edge. In certain embodiments, the frangible bonding agent may be disposed adjacent to the engaging member rather than on the engaging member so as to reduce or even eliminate any undesirable impact that the frangible bonding agent may have on the intended mechanical bonding function of the fastening system (e.g., fouling of the hooks). In certain embodiments, the frangible bonding agent may be disposed on a surface of the fastening system to which the engaging member is to be joined. For example, the frangible bonding agent may be applied to a nonwoven surface of an ear and/or fastening tab, such that when the fastening tab is folded the engaging member comes into contact with the frangible bonding agent. In certain embodiments, the frangible bonding agent may be disposed on both the engaging member and one or more other portions of the fastening system. For example, the frangible bonding agent may be applied as a single line of adhesive disposed on both the engaging member and a portion of the ear and/or fastening tab adjacent the engaging member. In another example, the frangible bonding agent may comprise a first line of adhesive disposed on the engaging member and a second line of adhesive disposed on another portion of the fastening system spaced apart from the first line and/or the engaging member. In yet another example, the frangible bonding agent may be formed by applying a first composition to a first portion of a substrate and a second composition to a second portion of the same substrate and then bringing the two portions of the substrate together, such that the two compositions contact one another and form a frangible bond. In this example, the first and second composition need not necessarily be capable of forming a frangible bond individually, as long as a frangible bond is formed when they are combined. Other suitable examples of patterns and configurations for applying the frangible bonding agent are described in U.S. Pat. No. 6,701,580 and U.S. Provisional Application Ser. No. 61/184,102.

Figure 4:
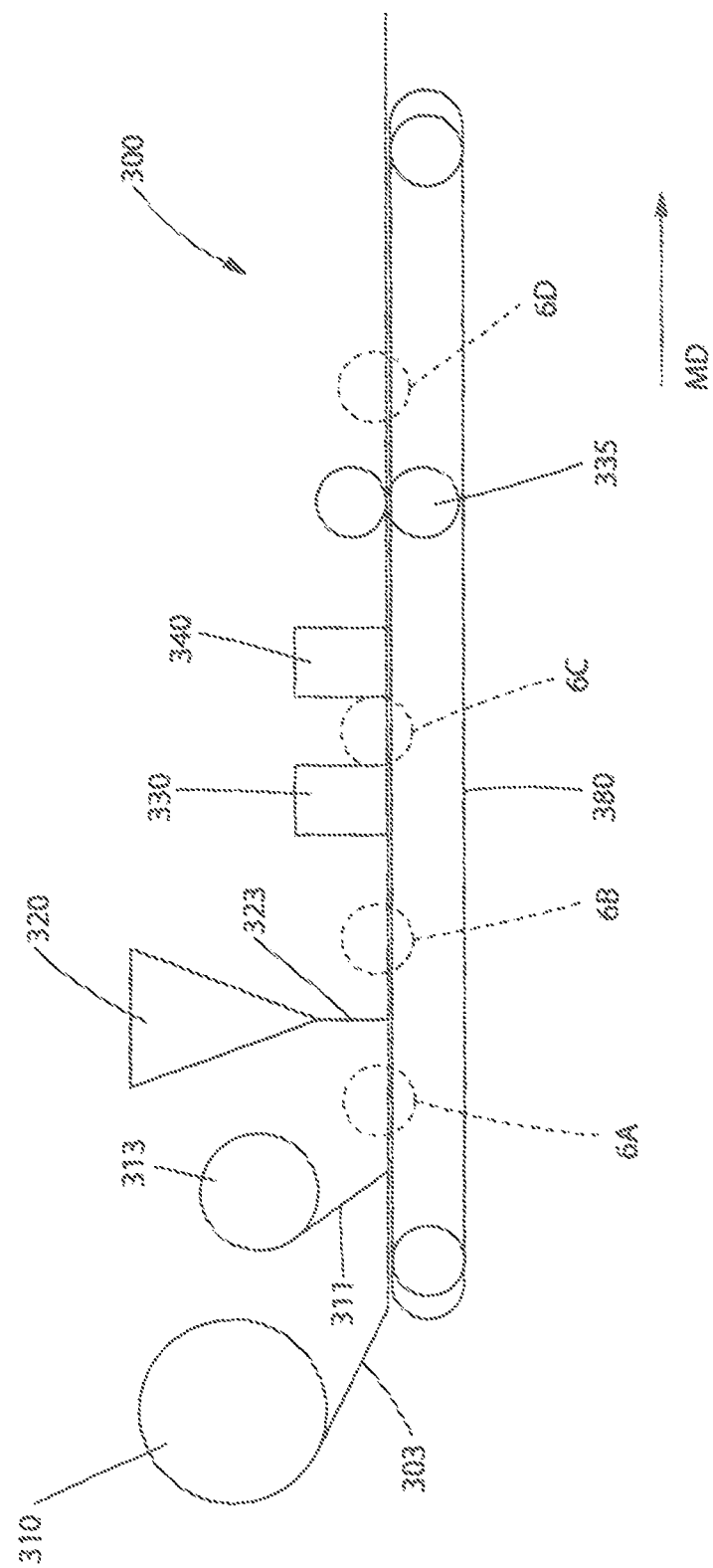
FIG. 4 is a diagram of a manufacturing process.

FIG. 4 shows an example of an exemplary high speed process 300 for folding a fastening system and maintaining the fastening system in a folded configuration. Elements 4A, 4B, 4C, and 4D, represented by broken-line circles, indicate particular positions in the process 300 that are shown in more detail in FIGS. 4A, 4B, 4C, and 4D, respectively. A substrate 303 is fed into the process 300, for example, by unwinding a continuous web from a supply roll 310 and placing the web on an endless conveying means 380 (e.g., a conveyor belt). In certain embodiments, the substrate 303 may be unwound from a roll and pulled into a converter with a combination of driven rollers, undriven rollers ("idlers"), and/or a rolling nip. In certain embodiments, the substrate 303 may be fed into the process 300 from one or more other upstream processes. The substrate 303 may be a single layer of nonwoven or film material or, alternatively, the substrate 303 may be a laminate material formed by joining one or more webs of material together in a face-to-face relationship. One particularly suitable example of a substrate 303 includes the stretchable laminate 410 illustrated in FIG. 6. The substrate 303 may be configured for use as a support member such as, for example, the support member 280 in FIG. 2. The conveying means 380 moves the substrate 303 in the MD to a position where engaging member material 311 is placed on the substrate 303 to form a composite web 308. The engaging member material 311 may be provided by a supply roll 313 or from an upstream process in the form of a continuous web of material or as discrete engaging members, and may be joined to the substrate 303 by any suitable means known in the art (e.g., adhesive bonding, cohesive bonding, ultrasonic bonding, thermal bonding, high pressure bonding, combinations of these and the like). The composite web 308 is moved in the MD to the bonding agent application station 320. At the bonding agent application station 320 a frangible bonding agent 323 is applied to the composite web 308. The frangible bonding agent 323 may be applied to one or more portions of the engaging member material 311 and/or the substrate 303. The frangible bonding agent 323 may be provided in the form of a fugitive hot-melt adhesive and may be applied by any suitable means known in the art (e.g., spraying, coating, slot-coating, extruding, meltblowing). For example, the frangible bonding agent 323 may be applied with an eDot brand hot-melt adhesive applicator, available from Nordson Corporation. The frangible bonding agent 323 may be applied as a relatively narrow continuous line or intermittent line having a width in the CD of between 0.1% and 30%; 1 and 25%; 1 and 15%; or even 1 and 10% of the width of the engaging member. the frangible bonding agent 323 may be applied as a continuous line having a length of between 1% and 100%; 1 and 50%; 1 and 40%; or even 1 and 20% of the length of the engaging member. Alternatively, the frangible bonding agent 323 may be applied as a series of 2 or more intermittent lines, each line having a length in the MD of between 1 mm and 50 mm. While FIG. 4 shows the process 300 as including only one bonding agent application station 320, it is to be appreciated that the process 300 may include more than one bonding agent application station 320 (e.g., 2, 3, 4, 5, or more) and/or the process 300 may include multiple applicators of the same or a different type in a single bonding agent application station 320 for applying the frangible bonding agent 323 in any pattern or combination of patterns desired. Downstream from the bonding agent application station 320 is a cutting station 330. At the cutting station 330, the composite web 308 may be separated into one or more discrete fasteners 355 or webs of fasteners 355. For example, the composite web 308 may be separated into two parallel webs of fasteners 355, as shown in FIG. 4C. The cutting station 330 may include a means for separating the composite web 308 into fasteners 355 having a particular shape or pattern (e.g., one or more knife rolls, reciprocating knives, scissors, plates, dies, embossing rolls, high pressure rolls, thermal cutters, ultrasonic cutters, laser cutters, or other known cutting tools or separating means). The cutting station 330 may also include a means for removing any excess or undesired material, which is sometimes referred to as trim or scrap, from the separated web. For example, the cutting station may use compressed air or vacuum to remove the trim from the moving line. Downstream from the cutting station 330 is a folding station 340 for folding the incoming webs of fasteners 355. In certain embodiments, the fasteners 355 are folded laterally inwardly at least once, such that the frangible bonding agent 323 contacts another portion of the fastener 355. Alternatively, the fasteners 355 may be folded two or more times. In certain embodiments, the folding station 340 may include a folding plow 341, as shown in FIG. 5. The folding plow 341 has a leading edge 342 for contacting the webs of fasteners 355 moving in the MD. When the webs of fasteners 355 contact the leading edge 342 of the folding plow 341, the fasteners 355 are moved to one side of the plow 341 or the other, depending on the orientation of the fastener. As the webs of opposing fasteners 355 move past their respective sides of the plow 341, a portion of each fastener 355 is folded over itself in the CD. Exemplary systems for folding various absorbent article components, including fasteners, are well known in the art (e.g., U.S. Pat. No. 5,714,027 issued to Taub). Upon exiting the folding station 340, the folded fasteners 355 pass through a pair of compression rolls 335, which apply pressure to the folded fasteners 355. The pressure applied by the compression rolls 335 tends to distribute the frangible bonding agent 323 across or into the component(s) that are to be bonded (e.g., by spreading the agent 323 across a surface or pushing the agent 323 further into a fibrous matrix). In certain embodiments, the compression rolls 335 may be used to at least partially engage complementary engageable members of a mechanical fastening system such as, for example, a hook/loop type mechanical fastening system. After being compressed, the webs of folded fasteners 355 may be spaced further away from one another in the CD and aligned with one another in the MD. In other words, opposing fasteners may be positioned to be directly across from each other in the CD, as opposed to the "staggered" positioning shown in FIGS. 4C and 4D). The webs of fasteners 355 may then be wound onto a roll or festooned into a box for later use or sent directly to a downstream process where they may be incorporated into an article.

Figure 4A:
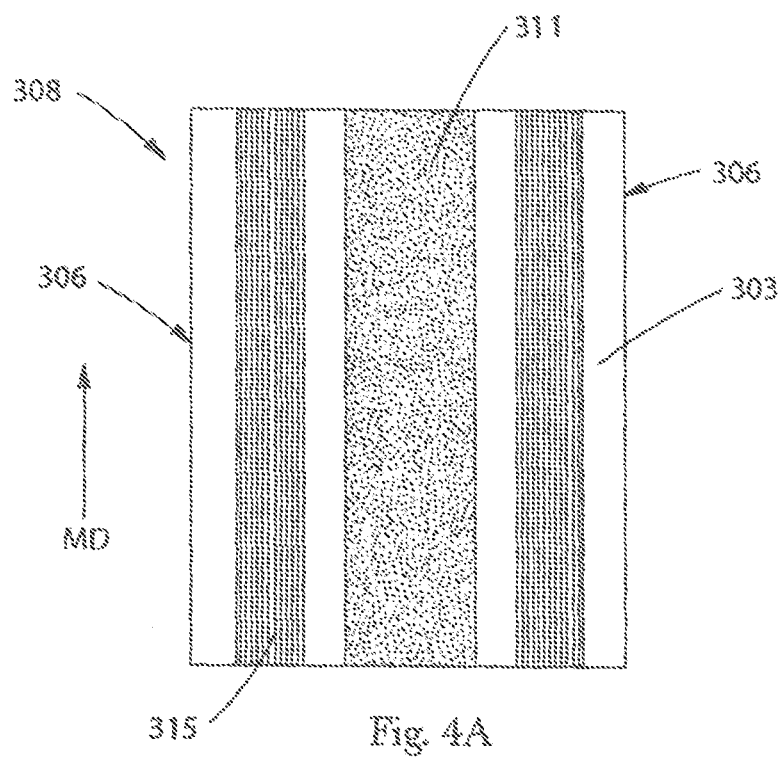
FIGS. 4A-4D are top plan views of a web at various points in a manufacturing process.
Figure 5:
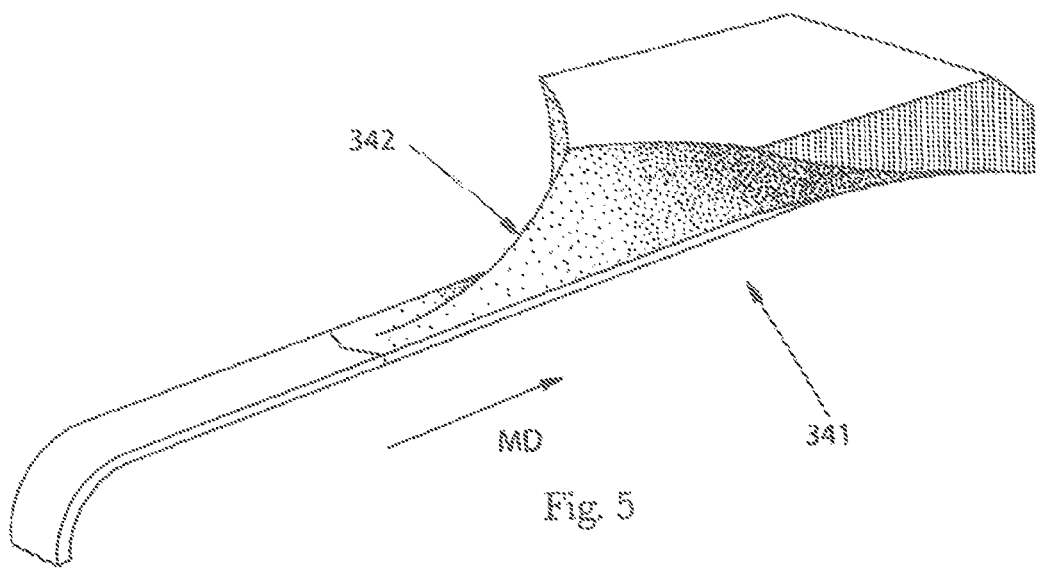
FIG. 5 is a perspective view of a folding plow.

FIG. 4A shows a composite web 308 at position 4A in the process 300 of FIG. 4. As seen in FIG. 4A, the substrate 303 has the engaging member material 311 joined thereto. The substrate 303 may include activated regions 315 for providing elastic extensibility in the CD. In certain embodiments, it may be desirable to position the engaging member material 311 to be substantially equidistant from the longitudinal side edges 306 of the substrate 303.

Figure 4B:
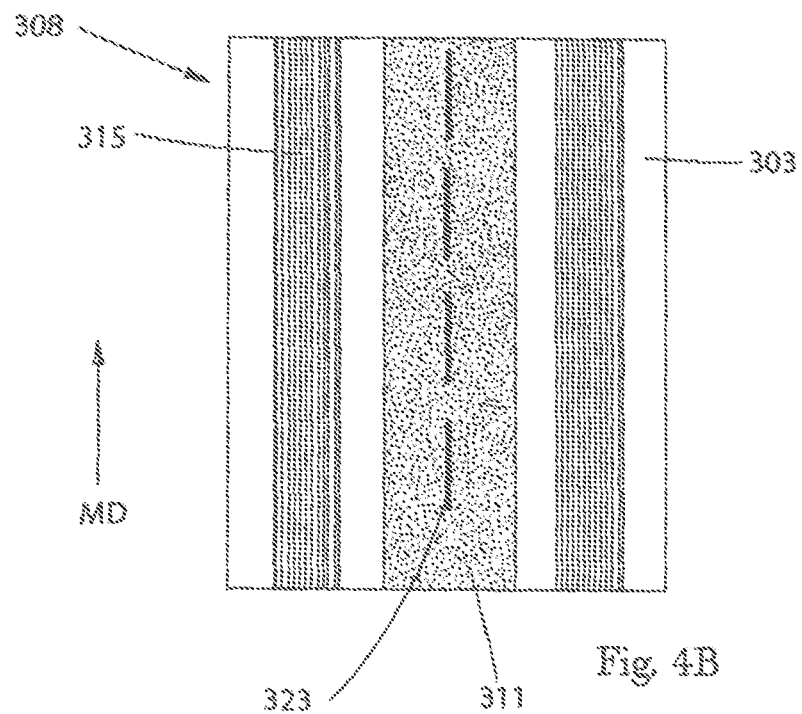
Figure 4C:
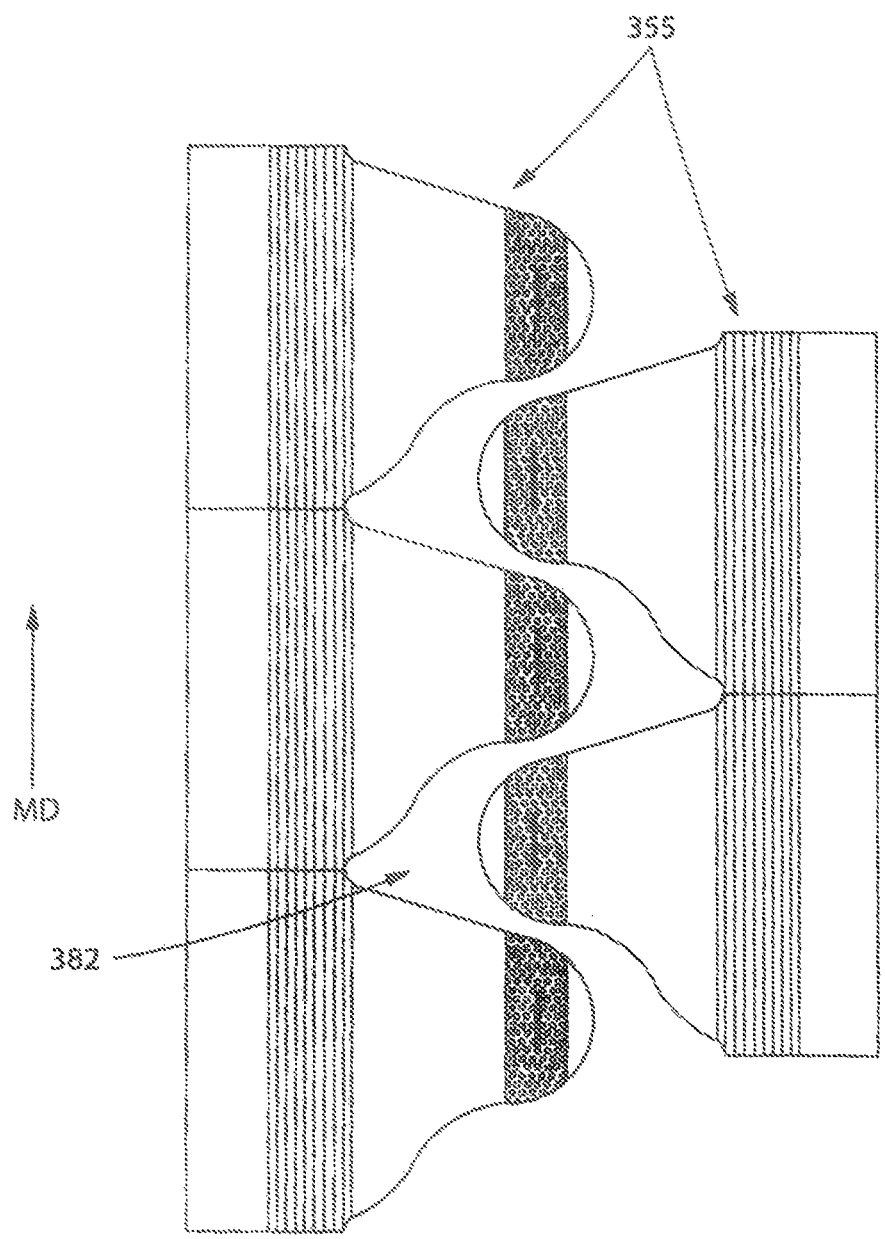

FIG. 4B shows a composite web 308 at position 4B in the process 300 of FIG. 4. As seen in FIG. 4B, a frangible bonding agent 323 has been applied to the engaging member material 311 in the form of an intermittent line comprising a plurality of line segments. Each line segment has a length in the MD and a width in the CD. While the bonding agent 323 is shown as being disposed on the engaging member material 311, it is to be understood that the bonding agent may also be applied to one or more portions of the activated region 315, substrate 303, or any other portion of the composite web 308, as desired.

FIG. 4C shows a composite web 308 at position 4C in the process 300 of FIG. 4. As seen in FIG. 4C, the composite web 308 has been separated into two parallel webs of fasteners 355. During the separation of the composite web 308, material (e.g., scrap or trim) is removed from the composite web 308 to form spaces 382 between the webs of fasteners 355. The webs of fasteners 355 are shown in FIG. 4C as being "staggered" or "offset" from one another in the MD. Alternatively, the parallel webs of fasteners 355 may be configured as mirror images of one another.

Figure 4D:
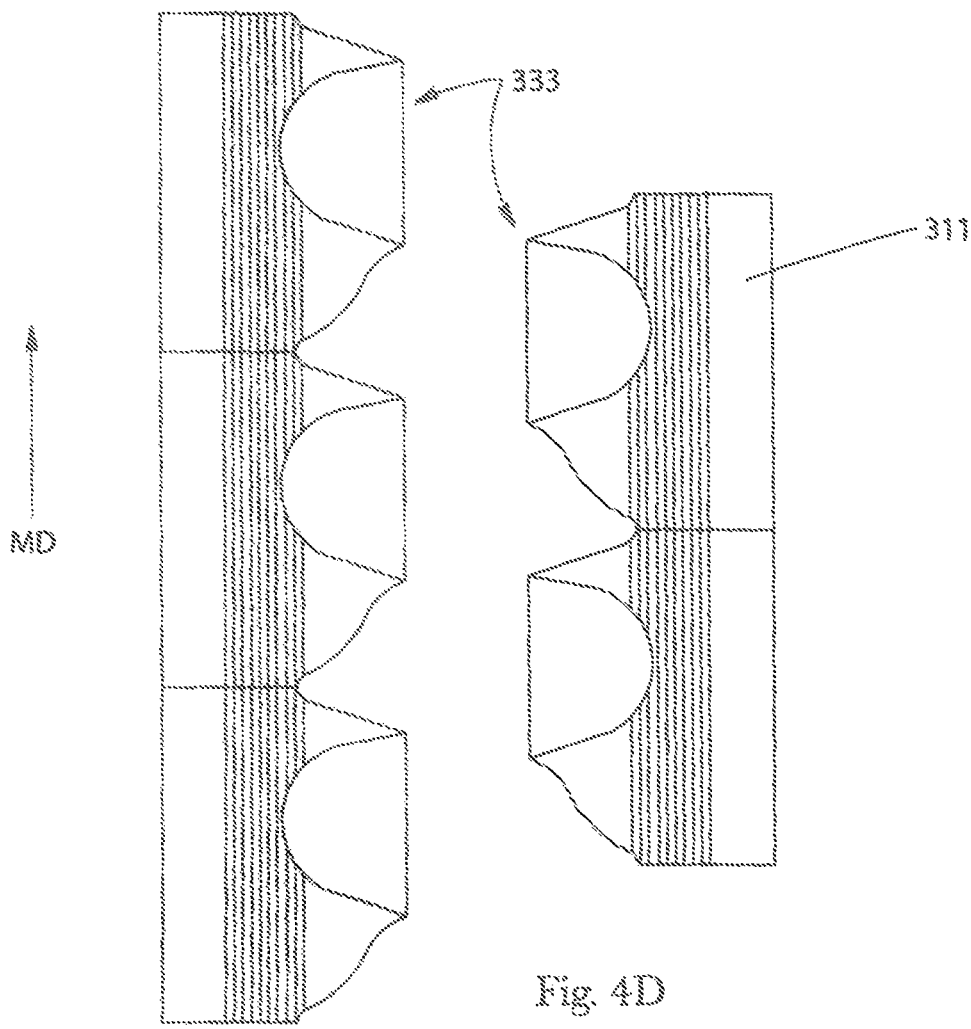

FIG. 4D shows a composite web 308 at position 4D in the process 300 of FIG. 4. As seen in FIG. 4D, The fasteners 355 have been folded laterally inwardly (i.e., in the CD), but are still staggered in the MD and in relative close proximity to one another.

Figure 6:
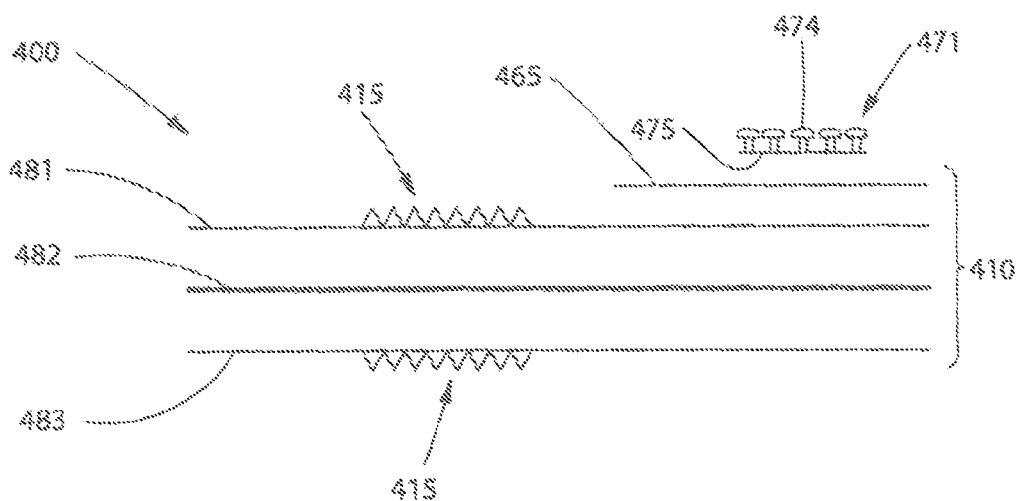
FIG. 6 is a schematic cross-section view of an ear for use in an absorbent article.

FIG. 6 shows an example of a substrate 400 suitable for use as an ear such as, for example, the ear 265 shown in FIG. 2. The substrate 400 may include a multi-layer laminate material 410 and an engaging member 471. The engaging member 471 may include one or more engaging elements 474 joined to a base 475. The engaging member 471 may be joined to the laminate material 410 by any suitable means known in the art. The laminate material 410 may include a first and second nonwoven layer 481 and 483. The first and second nonwoven layers 481 and 483 may be formed from any suitable plastic (i.e., extensible), elastic, or plasto-elastic fibers known in the art. Suitable materials for forming the fibers include natural and synthetic materials such as cellulose, cotton, rubber, extensible or elastic polyolefins (e.g., polypropylene, polyethylene, polybutylene), polyurethanes, nylon, combinations of these and the like. The fibers may be monocomponent or multi-component (e.g., core/shell, side-by-side, or sea/island type bicomponent fibers). One particularly suitable example of a fiber includes a core/shell type bicomponent fiber where the shell is formed from extensible polyethylene and the core is formed from an elastic polypropylene (e.g., VISTAMAXX brand polypropylene resin, available from Exxon Mobil Chemical). The nonwoven layers 481 and 483 may each be configured as a single layer of material or as a multi-layer laminate. For example, the first nonwoven layer 481 may be a layer of carded fibers having a basis weight of between 15 and 40 grams per square meter ("gsm"), and the second nonwoven layer 483 may be a three-layer SMS (i.e., spunbond-meltblown-spunbond) laminate having a total basis weight of between 8 and 30 gsm. One or both of the nonwoven layers 481 and 483 may include one or more activated portions 415, which provide some degree of elasticity and/or reduced resistance to stretch. The activated portions 415 may be provided by any suitable activation technique known in the art, such as one or more of the methods described in U.S. Pat. Nos. 4,200,963; 4,209,563; 4,525,407; 4,834,741; 5,143,679; 5,650,214; 5,156,793; 5,330,458; and 6,476,289. Sandwiched between the nonwoven layers 481 and 483 is a film layer 482. The film layer 482 may be formed from any suitable elastic or extensible material known in the art. In certain embodiments, the film 482 may be formed from an extensible material and subjected to a process for providing elasticity to the film 482, such as a commonly known SELFing process described in U.S. Pat. Nos. 5,518,801 and 5,554,145. The film layer 482 may be joined to one or both nonwoven layers 481 and/or 483 by any suitable means known in the art. The laminate material 410 may include an optional stiffener layer 465. The stiffener layer 465 may be formed from a high basis weight nonwoven such as, for example, a 30-100 gsm spunbond nonwoven. Suitable examples of stiffener layers are described, for example, in U.S. Publication Nos. 2007/0143972 and 2007/0157441.

In certain embodiments, a fastening system may include one or more discrete tape tabs that extend laterally outwardly from one or both longitudinal edges of the fastening system and/or the article comprising the fastening system. The tape tabs may be joined to a fastening system that is in turn joined to an article or, alternatively, the tabs may be joined directly to the article. The tape tabs generally include an engaging element that is configured to attach to a receiving element such as a commonly known landing zone. Suitable examples of tape tabs and ear configurations are disclosed in PCT Publications Nos. WO07/072421; WO07/072386; and WO07/069227; and U.S. Pat. No. 7,416,545.

Figure 7:
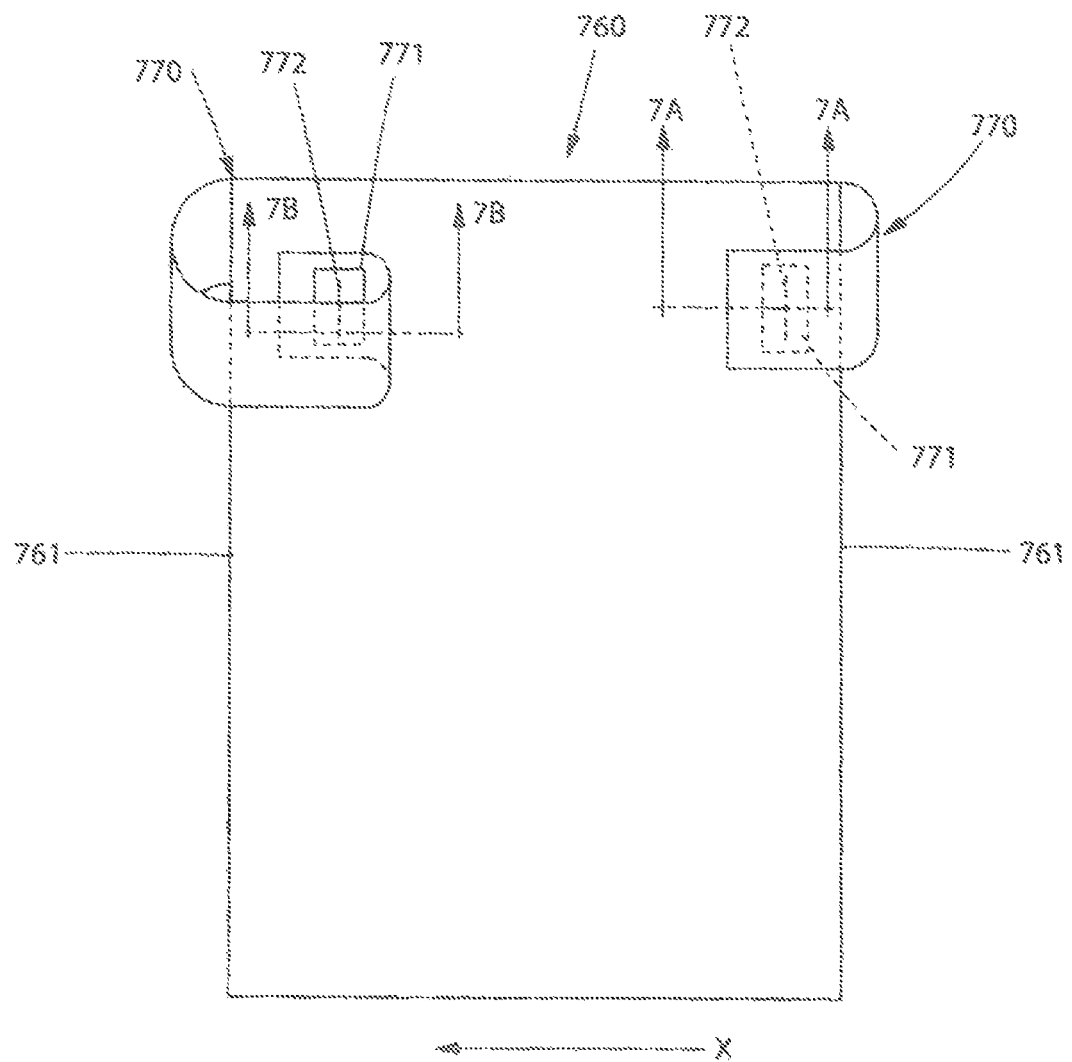
FIG. 7 is a top plan view of a disposable absorbent article.
Figure 7A:
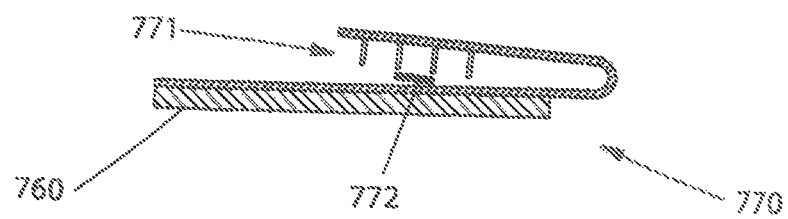
FIGS. 7A and 7B are schematic cross-section views of the fastening tab of FIG. 7.
Figure 7B:
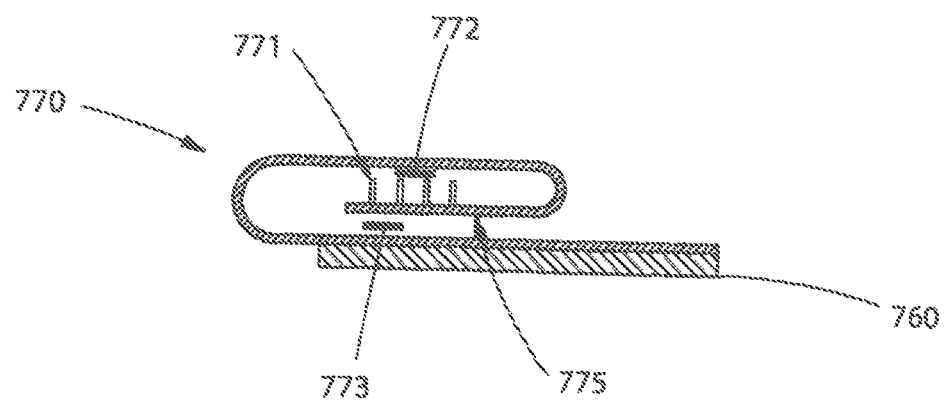

FIG. 7 shows an example of an absorbent article 760 that includes folded tape tabs 770 disposed along opposing longitudinal side edges 761 of the article 760. FIGS. 7A and 7B show the folded tape tabs 770 of FIG. 7 along lines A-A and B-B, respectively. When unfolded, the tape tabs 770 may extend laterally outwardly from the article 760 (i.e., in the x-direction). The tape tabs 770 may each include an engaging member 771 and a one or more frangible bonding agents 772. In the example shown in FIG. 7A, the tape tab 770 includes only one frangible bonding agent 772 disposed on the engaging member 771. The tape tab 770 of FIG. 7A may be folded laterally inwardly such that the frangible bonding agent 760 contacts a portion of the absorbent article 760 or another portion of the tape tab 770. In the example shown in FIG. 7B, a first frangible bonding agent 772 is disposed on the engaging member 771 and a second frangible bonding agent 772 is disposed on the non-engaging member side 775 of the tape tab 770. The tape tab 770 of FIG. 7B may be folded laterally inwardly, such that the first frangible bonding agent 772 contacts a first portion of the tape tab 770 or article 760 inboard of the engaging member. The tape tab 770 of FIG. 7B may then be folded laterally inwardly a second time such that the second bonding agent 772 contacts a second portion of the tape tab 770 or article 760 inboard of the first portion. It is to be understood that, with regard to FIGS. 7, 7A, and 7B the term inboard refers to the relative positions of elements when the article 760 and the tape tabs 770 are viewed in a flat-out configuration (i.e., not folded).

FIG. 8 shows another example of an absorbent article 860 comprising a pair of opposing tape tabs 870. The absorbent article 860 may also include one or more pair of opposing ears 865 to which the tape tabs 870 are joined, as shown in FIG. 8. The ear 865 may include an activated portion 890 that provides at least some elasticity or extensibility to the ear 865. The tape tab 870 may be joined to the ear 865 at a bonded portion 802 by any means known in the art (e.g., adhesive, pressure, thermal, or ultrasonic bonding). The tape tab 870 may include an engaging member 871 and a gripping portion 873. Broken-line circle 8A designates the portion of the tape tab 870 shown in FIG. 8A. As seen in FIG. 8A, the tape tab 870 may include a frangible bonding agent 872 disposed on the gripping member 873. Alternatively or additionally, the frangible bonding agent 872 may be applied to the middle portion 803 of the tape tab 870 or even the bonded portion 802.

Bonded Fastening System

The bond strength of an engaged fastening system that has been folded according to the process described herein may be characterized in terms of an opening force (Initial or Aged), a Modified Opening Force (Initial or Aged), or a shear force. Suitable values for Opening Force, Modified Opening Force, and Shear Force, as well as the method for measuring these values are described in U.S. Provisional Ser. No. 61/184,102. For example, a suitable Aged Modified Opening Force and/or Aged Opening Force for the fastening systems and/or frangible bonds described herein may be less than 8N; 5N; 2 N; 1.5 N; 1 N; 500 mN; or even less than 100 mN, but greater than 0 N. Table 1 below illustrates the crossover temperatures of several bonding agents. The first bonding agent is a fugitive hot-melt adhesive sold under the product code PHO-3005. The second bonding agent is a fugitive hot-melt adhesive sold under the product code PHO-3000. The third bonding agent is a permanent hot-melt adhesive sold under the product code D-3166. All three adhesives are available from H.B. Fuller. The crossover temperature of each bonding agent is determined according to the Rheological Measurement Test, except that the plate gap target is 1,789 µm for PHO-3000 and 1,743 µm for PHO-3005.

TABLE 1

| Bonding Agent | Crossover Temp ($T_x$) |
|---|---|
| PHO 3005 | 58-62° C. |
| PHO 3000 | 45-50° C. |
| D3166 | 73-77° C. |

Table 2 below illustrates the effect that temperature and/or pressure may have on the bond strength of an adhesive. PHO-3000 and PHO-3005 are both fugitive adhesives available from H. B. Fuller, while H2401 is a permanent bonding adhesive available from Bostik. For samples containing adhesive, the adhesive is applied to the center of the hook material shown in Table 3 (i.e., product code 963 from Aplix, product code XHK01084 from 3M, or product code XHK02897 from 3M) as a 15 mm continuous line having a nominal width of 1 mm in a direction substantially parallel to the MD. A sample of hook material that includes no fugitive adhesive is designated as "None" in Table 3 and is used as a control. The hook samples shown in Table 2 are attached to a diaper ear such as the diaper ear 265 illustrated in FIG. 2. In this example, the ear is an activated (i.e., incrementally stretched), four-layer laminate of a 65 micron film sandwiched between a layer of 27 gsm carded nonwoven and a layer of 17 gsm SMS nonwoven, and a 40 gsm spunbond nonwoven layer joined to the 27 gsm nonwoven layer. In order to obtain Aged Opening Force values, the samples are conditioned as follows. A first bifolded size 4 PAMPERS CRUISERS brand disposable diaper is placed at the bottom of a LEXAN brand polycarbonate box having a storage space that is 45 mm deep, 165 mm long and 125 mm wide. A second bifolded size 4 PAMPERS CRUISERS brand disposable diaper is placed on top of the first diaper in the container. The second diaper may contain up to five sample substrates (i.e., ears), which are placed inside the diaper (i.e., between the bifolded portions). Up to three sample containing diapers may be stacked on top of the bottom diaper in this fashion. A final bifolded size 4 PAMPERS CRUISERS brand disposable diaper is placed at the top of the stack of diapers in the box (for a total of up to five diapers). A lid is placed over the top of the stack of diapers and secured such that there is no gap between the lid and the top of the walls of the box. It is believed that this configuration simulates the typical storage pressure experienced by a diaper in a common flow wrap type package. The compressed samples are conditioned according to the temperatures and times shown in Table 3. The Initial Opening Force values shown in Table 3 are determined according to the Opening Force Test, within one hour after the adhesive shown in Table 3 is applied to the sample. The Aged Opening Force shown in Table 3 is obtained from samples that are conditioned as described above and subsequently tested according to the Opening Force Test.

Test Methods

Unless otherwise indicated, all test methods and material or sample conditioning are performed at a temperature of 23° C.±2° C. and a relative humidity of 50%±2%.

Opening Force Test

This method may be used for measuring the opening force of a first substrate bonded to a second substrate by determining the amount of force required to separate the substrate surfaces that are bonded to one another. The Opening Force Test is used to determine the Initial Opening Force value of a pair of bonded substrates by testing the pair of bonded substrates within one hour of the substrates being bonded to one another. The Opening Force Test is also used to determine the Aged Opening Force value of a pair of bonded substrates by testing the pair of bonded substrates more than 72 hours after the substrates are bonded to one another. The surface of a substrate that is opposite a bonded surface of that substrate is referred to in this method as a non-bonded surface. In certain embodiments, such as those including a folded substrate, the first substrate may be unitary with the second substrate. While this method may describe various exemplary configurations for bonded substrates, such as a diaper ear and/or fastening tab, it is to be understood that one of ordinary skill in the art could readily adapt this method to test the opening force of any bonded substrate.

The opening force of a bonded pair of substrates is measured using an MTS Alliance with TestWorks 4 software available from MTS Systems Corp., Eden Prairie, Minn., or equivalent, fitted with a suitable load cell. The load cell should be selected such that the maximum force attained in the test is between with 10% and 90% of the stated maximum load of the load cell. The jaws of the tensile tester must have flat surfaces and must be at least 25 mm wide. Also, the jaws should provide adequate force to ensure that the sample does not slip during testing. Additional details regarding suitable test apparatus, calibration procedures, etc. are given in ASTM D76-99 (Standard Specification for Tensile Testing for Textiles).

Sample Preparation:
1. If the bonded portion of the first and second substrates is incorporated into a finished product, carefully remove first and second substrates from the article (e.g., by cutting with scissors) while ensuring that there is substantially no peel or shear load on the bond to be tested.
2. If the sample contains exposed adhesive that is not a part of the bond between the first and second substrates, care must be taken to avoid allowing this adhesive to introduce artifacts into the data. Exposed adhesive should be deactivated, for example, by lightly coating it with talc or corn starch.

TABLE 2

| Adhesive | | Aplix 963 | | | 3M XHK01084 | | | 3M XHK02897 | | |
|---|---|---|---|---|---|---|---|---|---|---|
| | | Opening Force (N) | Standard Deviation | N | Opening Force (N) | Standard Deviation | N | Opening Force (N) | Standard Deviation | N |
| PHO-3005 | Initial: | 3.84 | 1.66 | 10 | 3.89 | 2 | 10 | 6.56 | 1.81 | 10 |
| | Aged: | 1.31 | 0.4 | 10 | 1.38 | 0.99 | 10 | 2.69 | 0.87 | 10 |
| PHO-3000 | Initial: | 3.77 | 2.75 | 10 | 4.11 | 3.08 | 10 | 7.97 | 2.1 | 10 |
| | Aged: | 1.18 | 0.4 | 10 | 1.48 | 0.6 | 10 | 1.64 | 0.33 | 10 |
| H2401 | Initial: | 3.73 | 0.44 | 10 | 5.84 | 0.72 | 10 | 5.19 | 1.15 | 10 |
| | Aged: | 4.84 | 1.01 | 10 | 7.04 | 0.9 | 10 | 6.44 | 0.78 | 10 |
| None | Initial: | 0.62 | 0.14 | 10 | 0.76 | 0.35 | 10 | 1.08 | 0.33 | 10 |
| | Aged: | 0.53 | 0.09 | 10 | 0.83 | 0.86 | 10 | 0.75 | 0.34 | 10 |

As can be seen from Table 2, only the fugitive adhesives provide a decrease in Hook Opening Force when aged, while the permanent bonding H2401 adhesive shows an undesirable increase in Hook Opening Force when aged.

Figure 9A:
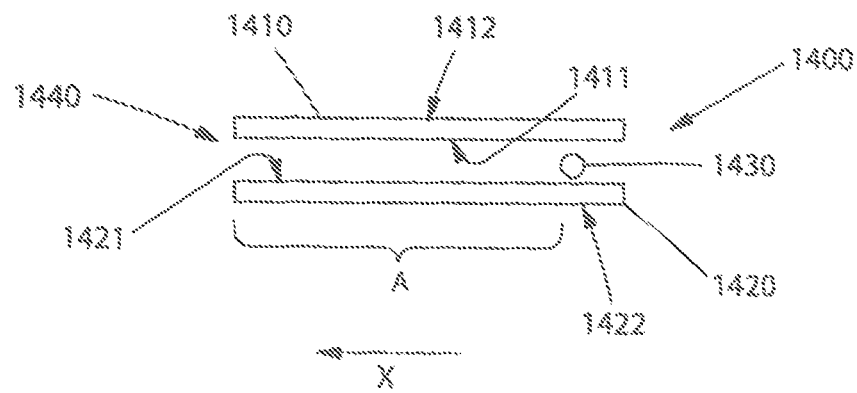
FIGS. 9A-9C are schematic cross-section views of a sample preparation for the Opening Force Test.
Figure 9B:
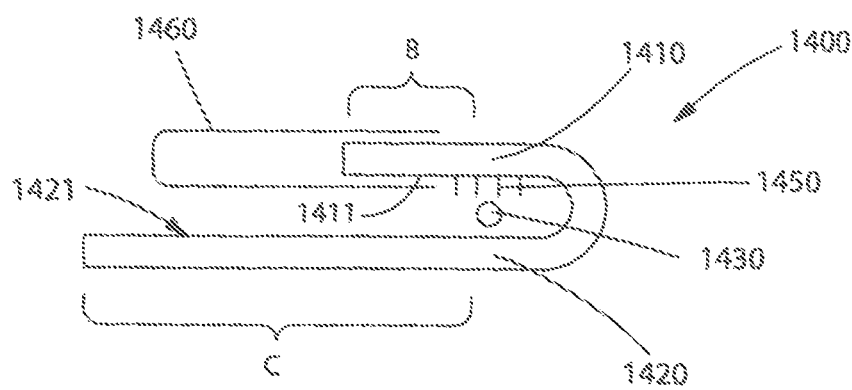
Figure 9C:
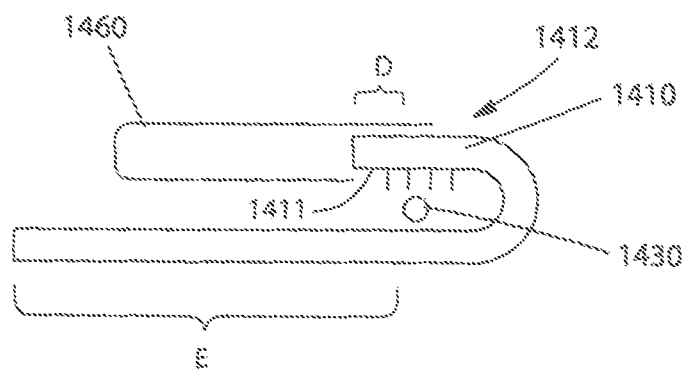

3. If either of the first or second substrates is extensible, render it substantially inextensible by applying backing tape (e.g., masking tape sold under the product code 410 by 3M) over the entire non-bonded surface of the material.
4. If the first and second substrates each extend at least 50 mm outwardly from the bond, then proceed to testing as detailed below. These extending portions are referred to as "tails." If the first and second substrates do not each have a tail that is at least 50 mm long, then make a tail by adding a leader made from standard, office masking tape such as SCOTCH 2600 brand masking tape available from 3M to the first and/or second sample substrate. To make a tail by attaching a leader, perform the following. Secure the tape to the non-bonded surface of the substrate such that the leader will extend at least 50 mm from the edge of the bond when the leader is folded back onto itself, for example, as shown in FIGS. 9B and 9C. Fold the leader 1460 back onto itself and join it to the bonded surface 1412 of the first substrate 1410 such that at least 5 mm of the leader 1460 overlaps itself and the bonded surface 1411. However, in any sample 1400 in which the bond is less than 10 mm from the relevant substrate edge, do not overlap the leader 1460 and the bonded surface 1411 of the substrate (i.e., only join the leader to itself as shown in FIG. 9C). FIG. 9A shows an example of a sample 1400 prepared without an added leader. The sample 1400 includes a first substrate 1410 having a bonded surface 1411 and a non-bonded surface 1412. The first substrate 1410 is bonded to a second substrate 1420, which also has a bonded surface 1421 and a non-bonded surface 1422. The first and second substrates 1410 and 1420 extend in the x-direction and are joined to one another by a bond 1430 (e.g., a frangible bond formed by a fugitive adhesive). In FIG. 9A, the distance A from the edge of the bond 1430 to the edge 1440 of the sample 1400 is greater than 50 mm. Thus, no leader is needed for the sample 1400 shown in FIG. 9A. FIG. 9B shows an example of a sample 1400 prepared with a leader 1460. In FIG. 9B, the exemplary sample 1400 includes a first and second substrate 1410 and 1420, respectively, that are unitary. That is, the first and second substrates 1410 and 1420 are formed from the same piece of material, for example, by folding the material over itself. The first substrate 1410 includes engaging elements 1450. The first substrate 1410 is joined to the second substrate 1420 by a frangible bond 1430 between the engaging elements 1450 and the bonded surface 1421 of the second substrate 1420. The distance B between the edge 1445 of the first substrate 1410 and the edge of the bond 1430, as shown in FIG. 9B, is greater than 10 mm but less than 50 mm. Thus, a leader 1460, which overlaps itself and the first substrate 1410, is affixed to the bonded side 1411 and the non-bonded side 1412 of the first substrate 1410. As shown in FIG. 9B, the leader 1460 does not overlap the engaging elements 1450 disposed on the bonded side 1411 of the first substrate 1410. The distance C from the edge of the bond 1430 to the edge 1455 of the second substrate 1420 is greater than 50 mm, and thus no leader is required. FIG. 9C shows an example of a sample 1400 prepared with no overlap between the leader 1460 and the bonded surface 1411 of the first substrate 1410. The distance D from the edge 1445 of the first substrate 1410 to the edge of the bond 1430, as shown in FIG. 9C, is less than 10 mm. In this case, a leader 1460 is affixed to the non-bonded side 1412 of the first substrate 1410 and then folded over such that the leader 1460 overlaps itself but not the bonded side 1411 of the first substrate 1410. The distance E from the edge of the bond 1430 to the edge 1455 of the second substrate 1420 is greater than 50 mm, and thus no leader 1460 is required.
5. If the sample extends more than 25 mm beyond the y-direction ends of the bond (see e.g., FIG. 2 for location of y-direction ends), the excess material is to be removed (e.g., cut off) in a manner which places substantially no shear or peel load on the bond to be tested.

Opening Force Testing of Prepared Sample.
1. Set the spacing of the tensile testers' jaws (gauge length), such that the jaws of both clamps are at least 25 mm from the edge of the bond, when the sample is mounted with a tail in each of the upper and lower jaws, and with the bonded portion extending laterally midway between the jaws. Position the sample in the jaws such that there is no substantial shear or peel force being applied to the bond to be tested. In addition, position the sample such that there is substantially equal distance between the bond and the upper and lower jaws.
2. Insert the tails into the respective jaws and ensure that the tails are centered in the jaws with no portion of the sample or leader extending beyond the grip. The sample should not be under tension, but should have minimal slack.
3. Ensure that the grips are suitably tight to prevent slippage, and zero the crosshead location.
4. Initiate the test at a crosshead speed of 305 mm/minute with collected into a data file at a resolution of approximately 10 data points per mm.
5. Data collection is to stop either 10 mm of crosshead travel after the bond is broken or immediately prior to encountering any obstruction which would obscure determining the force to break the bond. For example, an obstruction could be the fold of a folded tape tab or an unrelated bond between the first and second substrates such as a bond fusing the two substrates together.
6. If a leader tears or delaminates from the substrate to which it is attached prior to the bond breaking and the peak load force is greater than 8N, then record the observed peak load force. If a leader tears or delaminates from the substrate to which it is attached prior to the bond breaking and the peak load force is not greater than 8N, then discard the data and retest using a new sample, which has been reinforced by applying backing tape as described above.
7. Repeat the test until 10 samples have been successfully tested. Record the individual peak load forces and average them to obtain the Initial Opening Force value or Aged Opening Force value, as appropriate.

Coupon Peel Test

The object of this test is to measure the change in bond strength of a particular bonding agent over time as observed on a particular substrate. This method may be used to test the bond strength provided by a bonding agent harvested from a finished product or a virgin bonding agent (i.e., a bonding agent that has not been incorporated into an article).

Harvested Adhesive: Using a razor blade, small spatula, thermal knife, or other suitable tool, carefully remove adhesive to be tested from a finished product and place into a suitable container (e.g., by scraping or melting the adhesive off of the finished product and into a container such as a laboratory weigh boat or glass container). Care should be taken to minimize inclusion of substrate fragments, fastener fragments, or other contaminants in the sample to be tested. Check the sample prior to testing and remove any contaminants which may be present. Obtain sufficient adhesive to perform the test below (e.g., approximately 50 mg or 0.56 g per test run, depending on the test).

Virgin Adhesive: virgin adhesive obtained from a supplier may require homogenization before testing if the outer wrap is part of the adhesive formulation, which is not uncommon. If this is the case, melt the adhesive and wrapper together at 175° C. in the lab-oven. Stir the adhesive from time to time with a metal spatula by hand to homogenize. After homogenization pour the adhesive onto silicone-treated release paper and let it cool down to ambient temperature. If the adhesive does not require homogenization, then proceed directly to the test procedure.

Procedure

1. Prepare cut samples of 2 mil corona-treated PET film (polyethylene terephtalate) film (commercially available from Filmquest Group Inc, Bolingbrook, Ill. USA) by cutting the film into rectangular pieces of 65×100 mm.
2. Obtain two, flat, aluminum plates (12.7±2 mm thickness) and having dimensions of 150 mm×305 mm.
3. Pre-heat a Carver Press (e.g., model 3853-0 available from Carver Inc., Wabash, Ind. USA) and the two aluminum plates to 177° C. Stack the two aluminum plates one on top of the other with edges aligned on the bottom platen of the press and close the press to 345 MPa+/−690 kPa.
4. Pre-weigh 0.035-0.045 g of the harvested or virgin adhesive into a laboratory weigh boat or other suitable container
5. Obtain release paper (e.g., 40-pound release liner commercially available from American Coated Products, Zionsville, Ind. USA) sized such that the PET film samples can be placed entirely within the bounds of the release paper, but the release paper does not extend past the edges of the aluminum plates. Place a strip of the PET film corona-treated side up onto the release-coated side of a sheet of the release paper. Pour or place the adhesive onto the center of the PET film. Use a metal spatula to center the adhesive on the film.
6. Place a second strip of the PET film on top of the adhesive such that the corona-treated side of the PET film faces the adhesive. Place a second layer of release paper, release-coated side down, on top of the PET film-adhesive sandwich
7. Open the Carver press' platens sufficiently to remove the top aluminum plate, while leaving the bottom aluminum plate on the bottom platen of the press
8. Place the sample from step 5 onto the bottom aluminum plate, taking care to avoid dislocating the adhesive from its original position between the PET film layers.
9. Place the top aluminum plate on top of the paper-PET-adhesive sandwich disposed on the bottom aluminum plate. Use care to keep the sandwich of materials horizontal and avoid displacing the release paper and PET film in a way that could displace the adhesive from between the layers of PET film.
10. Close the Carver press platen to a pressure of 345 MPa+/−690 kPa. Wait 20 seconds. Then open the press to a sufficient gap to remove the stacked aluminum plates with the material sandwich still positioned between them. Again, keep the plates horizontal and use care to avoid displacing the release paper and PET film.
11. Gently remove the top plate and place the release paper-PET film-adhesive sandwich onto a horizontal room temperature surface.
12. Allow the sample to cool for at least 10 minutes but not more than 30 minutes then use a razor to cut just the PET/Adhesive sandwich into a 25 mm wide test specimen centered within the 65 mm PET width. The final test specimen is therefore 25×100 mm. Use care to avoid debonding the adhesive from the PET layers.
13. The peel force of the PET/Adhesive sandwich is measured using an MTS Alliance with TestWorks 4 software available from MTS Systems Corp., Eden Prairie, Minn., or equivalent, fitted with a suitable load cell. The load cell should be selected such that the maximum force attained in the test is between with 10% and 90% of the stated maximum load of the load cell. The jaws of the tensile tester are selected to have flat surfaces and are at least 25 mm wide. Also, the jaws should be configured or selected to provide adequate force to ensure that the sample does not slip during testing. Additional details regarding suitable test apparatus, calibration procedures, etc. are given in ASTM D76-99 (Standard Specification for Tensile Testing for Textiles).
14. Set the spacing of the tensile testers' jaws (gauge length) to 60+/−1 mm. Set the cross-head speed to 5.0 mm/min.
15. Mount the sample in the jaws of the tensile tester such that one PET strip is clamped in the top jaw and the other strip is clamped in the bottom jaw. Use the unbounded ends of the PET strips to do this while using care to avoid de-bonding the center of the strips from the adhesive. The sample should not be under tension, but should have minimal slack.
16. Ensure that the grips are suitably tight to prevent slippage, and zero the crosshead location.
17. Initiate the test at a crosshead speed of 5 mm/minute with collected into a data file at a resolution of approximately 10 data points per mm.
18. Data collection is to stop after the adhesive to PET bond is broken completely. Report the peak load during the test
19. Repeat the test until at least 3 samples have been successfully tested. Record the individual peak load forces and average them to obtain the Average Peel Force.

Rheological Measurement Test

The object of this test is to determine the crossover temperature of a composition. This method may be used to test an adhesive sample harvested from a finished product or a virgin adhesive sample. Refer to the Coupon Peel Test above for preparing virgin and harvested adhesive samples.

Equipment:

Air-circulating lab-oven or chamber capable to be controlled up to 200° C. (+/−3° C.) (e.g., Carbolite air circulating oven, Peak series, model PF60 with temperature control unit Eurotherm 2416CC)

Lab-Balance which allows precision of 0.01 g (e.g., Mettler PG503-S or equivalent)

TA Instruments Advanced Rheometer series AR2000 with Peltier temperature option, TA Instruments Corporation, New Castle, Del.; with 25 mm flat parallel plate geometry consisting of an upper steel plate (diameter: 25 mm) and a lower Peltier or heating plate enabling temperature control. The rheometer is capable of applying temperatures of from −5° C. to 170° C. with a precision of 0.5° C. and torques up to 200 milliNewton meters (mNm) with a precision of 0.1 mNm.

Test Procedure:

Geometry Gap Setting:
1. Set the temperature of the Peltier or heating plate of the rheometer to 120° C.
2. Calibrate the zero gap at 120° C.
3. Set the geometry gap to 2000 micrometers.
4. Weigh out 0.56 g+/−0.01 g of adhesive and place it onto the center of the Peltier or heating plate of the rheometer and set the temperature to 120° C.
5. After approximately ⅔ of the amount of adhesive is molten, slowly lower the upper plate to the geometry gap of 2000 micrometer. The velocity of the rheometer head must not exceed 1000 micrometers per second in order to achieve good contact between the adhesive and the upper plate without damaging the adhesive sample.
6. Cover the geometry with the geometry cover—i.e., solvent trap cover—for 2 minutes so that the upper plate can heat up and the adhesive gets completely molten.
7. Remove the cover and rotate the upper plate manually to distribute the adhesive evenly between the upper plate and the Peltier or heating plate. Ensure full contact of the adhesive to the upper plate. Afterwards cover the geometry again for another 2 minutes.
8. Remove the cover and check whether the adhesive is distributed evenly. If it is not, repeat point 7. If it is, cover the geometry again and continue with point 9.
9. Perform a pre-shearing at a frequency of 2.5 radians per second and an oscillatory strain amplitude of 1% for 4 minutes to condition the adhesive.
10. After pre-shearing keep the temperature at 120° C. for 1 minute to let the adhesive settle and recover from pre-shearing.
11. Ensure the geometry and adhesive are thermally equilibrated by maintaining the setup at 120° C. for more than 2 minutes without any application of stress.

Temperature Sweep Execution:

Perform a temperature sweep starting at 120° C. and cooling down to −5° C. at a cooling rate of 3° C. per minute. Set the frequency to 10 radians per second and the commanded oscillatory strain amplitude to 26%. The apparent storage modulus (G'), apparent loss modulus (G") and the apparent loss tangent (Tan δ) are recorded as a function of temperature. Note that the commanded strain may not be achieved, especially at lower temperatures, and that the strain may exceed the linear elastic region of the adhesive composition. The apparent values are the respective values recorded by the instrument notwithstanding these conditions.

Calculation/Reporting:

From the temperature sweep report the following parameters: cross-over temperature in ° C. (1 decimal place). The cross-over-temperature is found at the end of the rubber-plateau towards higher temperatures indicating the beginning of the terminal zone. At the cross-over temperature, the apparent storage modulus and apparent loss modulus values are equal and the apparent loss tangent value is 1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for folding a fastener during a high speed manufacturing process and maintaining the folded fastener in a folded configuration throughout the high speed manufacturing process, the method comprising:
    obtaining an article comprising a foldable fastener and moving the article in a machine direction during the high speed manufacturing process, the high speed manufacturing process having a cross direction orthogonal to the machine direction, the foldable fastener comprising a web with first and second opposing surfaces, and at least one engaging member joined to the web;
    applying a frangible bonding agent that comprises a fugitive adhesive to a first portion of the first surface of the fastener; and
    folding the fastener such that the frangible bonding agent contacts a second portion of the first surface of the fastener; and
    wherein the fastener is a hook/loop type mechanical fastener;
    wherein the engaging member includes a plurality of hooks with gaps between adjacent hooks, and the web includes a plurality of receiving elements that are engageable with the hooks; and
    wherein the frangible bonding agent forms a substantially unbroken line that penetrates at least partially into one or more of the gaps between adjacent hooks.

2. The method of claim 1, wherein the folded fastener has an Initial Opening Force value of greater than about 2 N according to the Opening Force Test.

3. The method of claim 1, wherein the folded fastener has an Aged Opening Force value of less than about 8 N.

4. The method of claim 1, wherein the fastener is folded such that the frangible bonding agent contacts a second portion of the first surface of the fastener and forms a bond between the first and second portions of the first surface.

5. The method of claim 1, wherein the fastener is folded in the cross direction along a line extending in the machine direction.

6. The method of claim 5, wherein the folded fastener is subjected to compression.

7. The method of claim 1, wherein the fastener includes a fastening tab and the engaging member is disposed on the fastening tab.

8. The method of claim 1, wherein the engaging member is joined to the fastener at a base and the frangible bonding agent is not applied to the base.

9. The method of claim 1, wherein the frangible bonding agent is applied in a pattern selected from the group consisting of one or more substantially straight lines, an s-shape, a z-shape, a c-shape, a broken line, a t-shape, a cross-shape, spiral-shape, omega-shape, dots and combinations of these.

10. The method of claim 1, wherein the fugitive adhesive has a strength decay of between about 20%, and 100% according to the Coupon Peel Test.

11. The method of claim 1, wherein the fugitive adhesive has a strength decay of between about 30% and 70% according to the Coupon Peel Test.

* * * * *